United States Patent [19]

Kelly

[11] 4,169,841

[45] Oct. 2, 1979

[54] ALKENYL-SUBSTITUTED 9-DEOXY-6,9-α-EPOXYMETHANO-PG ANALOGS

[75] Inventor: Robert C. Kelly, Kalamazoo, Mich.

[73] Assignee: The Upjohn Company, Kalamazoo, Mich.

[21] Appl. No.: 941,815

[22] Filed: Sep. 11, 1978

Related U.S. Application Data

[62] Division of Ser. No. 788,145, Apr. 19, 1977, Pat. No. 4,130,569.

[51] Int. Cl.² ............................................. C07D 311/02
[52] U.S. Cl. .................................................... 260/345.2
[58] Field of Search ...................................... 260/345.2

[56] References Cited

U.S. PATENT DOCUMENTS 4,123,441   10/1978   Johnson ........................... 260/345.2

OTHER PUBLICATIONS

Pace-Asciak et al., Biochem., 10, 3657 (1971).
Pace-Asciak et al., JACS, 98, 2348 (1976).

*Primary Examiner*—Nicky Chan
*Attorney, Agent, or Firm*—Morris L. Nielsen

[57] ABSTRACT

Processes for preparing prostacyclin analogs which are 9-deoxy-6,9-epoxymethano derivatives of prostaglandin $F_{1\alpha}$-type compounds, illustrated, for example, by a compound of the formula

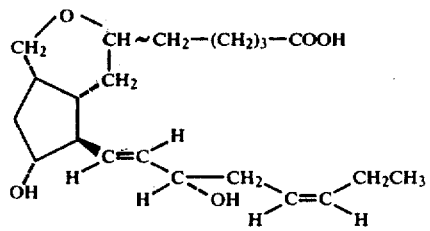

wherein ~ indicates alpha or beta configuration; including the products and intermediates produced therein, said products having pharmacological utility.

10 Claims, No Drawings

ALKENYL-SUBSTITUTED 9-DEOXY-6,9-α-EPOXYMETHANO-PG ANALOGS

CROSS REFERENCE TO RELATED APPLICATIONS

This application is a division of copending application Ser. No. 788,145, filed Apr. 19, 1977, now issued as U.S. Pat. No. 4,130,569.

BACKGROUND OF THE INVENTION

This invention relates to products having prostacyclin-like structure and to processes for preparing them. In particular this invention relates to 5,6-dihydro-prostacyclin analogs and to processes for preparing them.

Prostacyclin is an organic compound related to prostaglandins and identified as 9-deoxy-6,9α-epoxy-$\Delta^5$-PGF$_{1\alpha}$. It is particularly characterized as an enol ether from its chemical properties. See R. A. Johnson et al., Prostaglandins 12, 915 (1976).

The prostaglandins and analogs are well-known organic compounds derived from prostanoic acid which has the following structure and atom numbering:

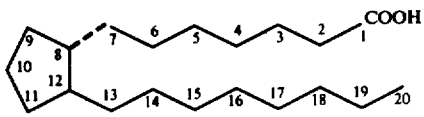

As drawn hereinafter the formulas represent a particular optically active isomer having the same absolute configuration as PGF$_{1\alpha}$ obtained from mammalian tissues.

In the formulas, broken line attachments to the cyclopentane ring or side chain indicate substituents in alpha configuration, i.e. below the plane of the ring or side chain. Heavy solid line attachments indicate substitutents in beta configuration, i.e. above the plane.

Somewhat related compounds have been reported by C. Pace-Asciak et al., in Biochemistry, Vol. 10, pages 3657–3664 (1971), including, for example:

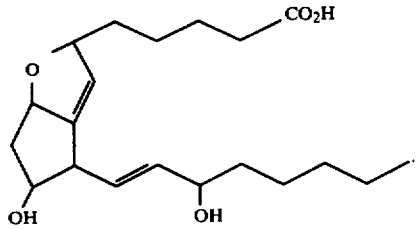

Prostacyclin and prostacyclin-type compounds, including derivatives and analogs, are extremely potent in causing various biological responses. For that reason, these compounds are useful for pharmacological purposes. A few of those biological responses are: inhibition of blood platelet aggregation, stimulation of smooth muscle, inhibition of gastric secretion and reduction of undesirable gastrointestial effects from systemic administration of prostaglandin synthetase inhibitors.

Because of these biological responses, prostacyclin and prostcyclin-type compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits, and monkeys.

Prostacyclin and prostacyclin-type compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The addition of prostacyclin and prostacyclin-type compounds to whole blood provides in vitro applications such as storage of whole blood to be used in heart-lung machines. Additionally whole blood containing these compounds can be circulated through limbs and organs, e.g. heart and kidneys, whether attached to the original body, detached and being preserved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused body portion, attached or detached, to the recipient, or to two or all of those at a total steady state dose of about 0.001–1.0 μg./ml. of whole blood. These compounds are also useful in preparing platelet-rich concentrates from blood for use in treating thrombocytopenia or in chemotherapy.

Prostacyclin and prostacyclin-type compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 μg. per kg. of body weight per weight until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

Prostacyclin and prostacyclin-type compounds are also useful in mammals, including man and certain useful animals, e.g. dogs and pigs, to reduce and control excessive gastric secretion, thereby reduce or avoid gastrointestinal ulcer formation, and accelerate the healing of such ulcers alredy present in the gastrointestinal tract. For this purpose, these compounds are injected or infused intravenously, subcutaneously, or intramuscularly in an infusion dose range about 0.1 µg. per kg. of body weight per minute, or in a total daily dose by injection or infusion in the range about 0.1 to about 10 mg. per kg. of body weight per day, the exact dose depending on the age, weight, and condition of the patient or animal, and on the frequency and route of administration.

Prostacyclin and prostacyclin-type compounds are also useful in reducing the undesirable gastrointestinal effects resulting from systemic administration of anti-inflammatory prostaglandin synthetase inhibitors, and are used for that purpose by concomitant administration of the prostacyclin or prostacyclin-type compound and the anti-inflammatory prostaglandin synthetase inhibitor. See Partridge et al., U.S. Pat. No. 3,781.429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. Prostacyclin and prostacyclin-type compounds are useful, for example, in reducing the undesirable gastrointestinal effects resulting from systemic administration of indomethacin, phenylbutazone, and aspirin. These are substances specifically mentioned in Partridge et al., as non-steroidal, anti-inflammatory agents. These are also known to be prostaglandin synthetase inhibitors.

The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration.

The prostacyclin or prostacyclin-type compound is administered along with the anti-inflammatory prostaglandin synthetase inhibitor either by the same route of administration or by a different route. For example, if the anti-inflammatory substance is being administered orally, the prostacyclin or prostacyclin-type compound is also administered orally, or, alternatively, is administered rectally in the form of a suppository or, in the case of women, vaginally in the form of a suppository or vaginal device for slow release, for example as described in U.S. Pat. No. 3,545,439. Alternatively, if the anti-inflammatory substance is being administered rectally, the prostacyclin or prostacyclin-type compound is also administered rectally. Further, the prostacyclin derivative can be conveniently administered orally or, in the case of women, vaginally. It is especially convenient when the administration route is to be the same for both anti-inflammatory substance and prostacyclin or prostacyclin-type compound to combine both into a single dosage form.

The dosage regimen for the prostacyclin or prostacyclin-type compound in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular prostacyclin or prostacyclin-type compound to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostacyclin or prostacyclin-type compound to reduce and then substantially to eliminate those undesirable effects.

Prostacyclin or prostacyclin-type compounds are also useful in the treatment of asthma. For examle, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use the prostacyclin or prostacyclin-type compound can be combined advantageously with other anti-asthmatic agents, such as sympathmimetics (isoproterenol, phenylephrine, ephedrine, etc.); xanthine derivatives (theophylline and aminophylline); and corticosteroids (ACTH and prednisolone).

Prostacyclin or prostacyclin-type compounds are effectively administered to human asthma patients by oral inhalation or by aerosol inhalation.

For administration by the oral inhalation route with conventional nebulizers or by oxygen aerosolization it is convenient to provide the prostacyclin ingredient in dilute solution, preferably at concentrations of about 1 part of medicament to about 100 to 200 parts by weight of total solution. Entirely conventional additives may be employed to stabilize these solutions or to provide isotonic media, for example, sodium chloride, sodium citrate, citric acid, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No 2,868,691 for example.

Prostacyclin or prostacycli-type compounds are useful in mammals, including man, as nasal decongestants and are used for this purpose in a dose range of about 10 µg. to about 10 mg. per ml. of a pharmacologically suitable liquid vehicle or as an aerosol spray, both for topical application.

Prostacyclin or prostacyclin-type compounds are also useful in treating peripheral vascular disease in humans. The term peripheral vascular disease as used herein means disease of any of the blood vessels outside of the heart and to disease of the lymph vessels, for example, frostbite, ischemic cerebrovascular disease, arteriovenous fistulas, ischemic leg ulcers, phlebitis, venous insufficiency, gangrene, hepatorenal syndrome, ductus arteriosus, non-obstructive mesenteric ischemic, arteritis lymphangitis and the like. These examples are included to be illustrative and should not be construed as limiting the term peripheral vascular disease. For these conditions the prostacyclin compounds are administered orally or parenterally via injection or infusion directly into a vein or artery, intra-venous or intra-arterial injections being preferred. The dosages of these compounds are in the range of 0.01–1.0 μg. administered by infusions at an hourly rate or by injection on a daily basis, i.e. 1–4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed.

Prostacyclin or prostacyclin-type compounds are accordingly useful for treating peripheral vascular diseases in the extremities of humans who have circulatory insufficiencies in said extremities, such treatment affording relief of rest pain and induction of healing of ulcers.

For a complete discussion of the nature of and clinical manifestations of human peripheral vascular disease and the method previously known of its treatment with prostaglandins see South African Pat. No 74/0149 referenced as Derwent Farmdoc No. 58,400V. See Elliott, et al., Lancet, Jan. 18, 1975, pp. 140–142.

Prostacyclin or prostacyclin-type compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

Prostacyclin or prostacyclin-type compounds are further useful for controlling the reproductive cycle in menstruating female mammals, including humans. By the term menstruating female mammals is meant animals which are mature enough to menstruate, but not so old that regular menstruation has ceased. For that purpose the prostacyclin compound is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

Prostacyclin or prostacyclin-type compounds are further useful in causing cervical dilation in pregnant and non-pregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostacyclin compounds is also useful in operative gynecology such as D and C (Cervical Dilation and Uterine Curettage) where mechanical dilation may cause performation of the uterus, cervical tears, or infections. It is also useful for diagnostic procedures where dilation is necessary for tissue examination. For these purposes, the prostacyclin compound is administered locally or systemically.

The prostacyclin compound, for example, is administered orally or vaginally at doses of about 5 to 50 mg. per treatment of an adult female human, with from one to five treatments per 24 hour period. Alternatively the compound is administered intramuscularly or subcutaneously at doses of about one to 25 mg. per treatment. The exact dosages for these purposes depend on the age, weight, and condition of the patient or animal.

Prostacyclin and prostacyclin-type compounds are further useful in domestic animals as in abortifacients (especially for feedlot heifers), as an aid to estrus detection, and for regulation or synchronization of estrus. Domestic animals include horses, cattle, sheep, and swine. The regulation or synchronization of estrus allows for more efficient management of both conception and labor by anabling the herdsman to breed all his females in short pre-defined intervals. This synchronization results in a higher percentage of live births than the percentage achieved by natural control. The prostacyclin compound is injected or applied in a feed at doses of 0.1–100 mg. per animal and may be combined with other agents such as steroids. Dosing schedules will depend on the species treated. For example, mares are given the prostacyclin compound 5 to 8 days after ovulation and return to estrus. Cattle are treated at regular intervals over a 3 week period to advantageously bring all into estrus at the same time.

Prostacyclin or prostacyclin-type compounds increase the flow of blood in the mammalian kidney, thereby increasing volume and electrolyte content of the urine. For that reason, these compounds are useful in managing cases of renal dysfunction, especially those involving blockage of the renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 μg. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2mg per kg. of body weight per day.

These prostacyclin or prostacyclin-type-compounds are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness or noticeably but incompletely cleared or completely cleared.

For those purposes, these compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or perilesionally, or subcutaneously, using appropriate sterile saline compositions.

Prostacyclin or prostacyclin-type compounds are useful as antiinflammatory agents for inhibiting chronic inflammation in mammals including the swelling and other unpleasant effects thereof using methods of treatment and dosages generally in accord with U.S. Pat. No. 3,885,041, which patent is incorporated herein by reference.

SUMMARY OF THE INVENTION

It is the purpose of this invention to provide novel products having pharmacological activity. It is a further purpose to provide processes for preparing these products and their intermediates.

The presently provided cyclic ethers include compounds within the scope of the generic formula:

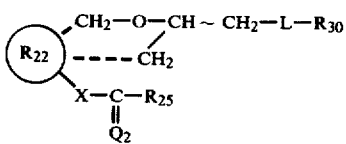

wherein L is (1) a valence bond, (2) —(CH$_2$)$_d$—wherein d is one to 5 inclusive, (3) —(CH$_{2t}$)$_t$—CF$_2$—wherein t is 2, 3, or 4, (4) —CH$_2$—CH=CH—A—wherein A is a valence bond or —(CH$_2$)$_h$— wherein h is one, 2, or 3, or (5) —(CH$_2$)$_n$—O—CH$_2$—Y—wherein Y is a valence bond or —(CH$_2$)$_k$—wherein k is one or 2, and wherein n is zero or one; wherein Q$_2$ is

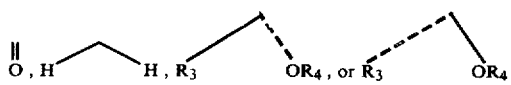

wherein R$_3$ is hydrogen or alkyl of one to 4 carbon atoms, inclusive, and wherein R$_4$ is hydrogen, tetrahydropyranyl, tetrahydrofuranyl, 1-ethoxyethyl or a group of the formula

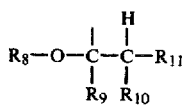

wherein R$_8$ is alkyl of one to 18 carbon atoms, inclusive cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein R$_9$ and R$_{10}$ are the same or different, being hydrogen, alkyl of one to 4 carbon atoms, inclusive, phenyl or phenyl substituted with one, 2, or 3 alkyl of one to 4 carbon atoms, inclusive, or, when R$_9$ and R$_{10}$ are taken together, —(CH$_2$)$_a$—or —(CH$_2$)$_b$—O—(CH$_2$)$_c$—wherein a is 3, 4, or 5, b is one, 2, or 3, and c is one, 2, or 3 with the proviso that b plus c is 2, 3, or 4, and wherein R$_{11}$ is hydrogen or phenyl; wherein R$_{22}$ is

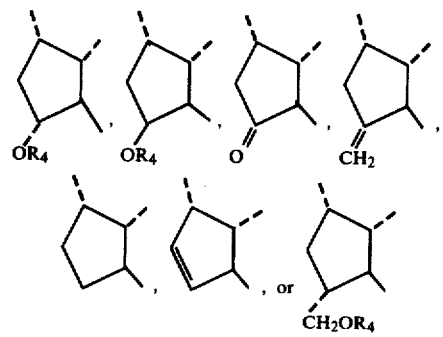

wherein R$_4$ is as defined above; wherein R$_{25}$ is

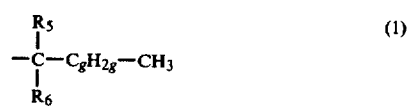

wherein C$_g$H$_{2g}$ is alkylene of one to 9 carbon atoms, inclusive, with one to 5 carbon atoms, inclusive, in the chain between —CR$_5$R$_6$—and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro;

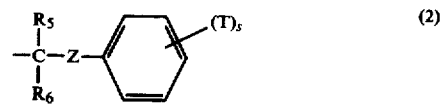

wherein R$_5$ and R$_6$ are as defined above with the proviso that neither R$_5$ nor R$_6$ is fluoro when Z is oxa (—O—); wherein Z represents an oxa atom (—O—) or C$_j$H$_{2j}$wherein C$_j$H$_{2j}$is a valence bond or alkylene of one to 9 carbon atoms, inclusive, substituted with zero, one, or 2 fluoro, with one to 6 carbon atoms, inclusive between —CR$_5$R$_6$—and the phenyl ring; wherein T is alkyl of one to 4 carbon atoms, inclusive, fluoro, chloro, trifluoromethyl, or —OR$_7$—wherein R$_7$ is alkyl of one to 4 carbon atoms, inclusive, and s is zero, one, 2, or 3, with the proviso that not more than two T's are other than alkyl and when s is 2 or 3 the T's are either the same or different; or

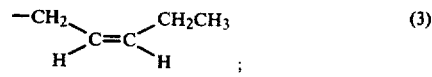

wherein R$_{30}$ is
(1) —COOR$_{19}$
(2) —CH$_2$OH
(3) —CH$_2$N(R$_{18}$)$_2$

-continued or

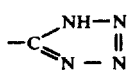 (5)

wherein $R_{19}$ is (a) alkyl of one to 12 carbon atoms, inclusive, (b) cycloalkyl of 3 to 10 carbon atoms, inclusive, (c) aralkyl of 7 to 12 carbon atoms, inclusive, (d) phenyl, (e) phenyl substituted with one, 2, or 3 chloro or alkyl of one to 4 carbon atoms, inclusive,

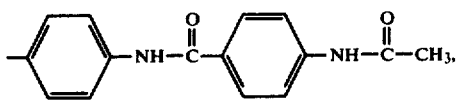 (f)

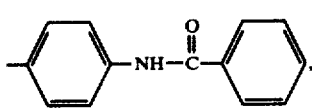 (g)

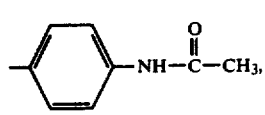 (h)

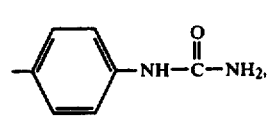 (i)

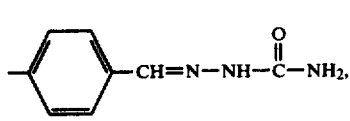 (j)

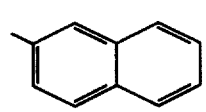 (k)

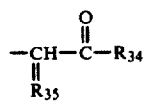 (l)

$$-CH-\overset{O}{\underset{R_{35}}{C}}-R_{34}$$

wherein $R_{34}$ is phenyl, p-bromophenyl, p-biphenylyl, p-nitrophenyl, p-benzamidophenyl, or 2-naphthyl, and wherein $R_{35}$ is hydrogen or benzoyl, or (m) hydrogen, or (n) a pharmacologically acceptable cation; and wherein $R_{18}$ is hydrogen, alkyl of one to 12 carbon atoms, inclusive, benzyl, or phenyl, being the same or different;

wherein X is cis- or trans-CH=Ch—, C≡C—, or —CH$_2$CH$_2$—; and wherein ~ indicates attachment in cis or trans configuration; including the lower alkanoates thereof.

By way of illustration, formula III represents 9-deoxy-6ξ,9α-epoxymethano-2,3,4-trinor-PGF$_1$, methyl ester, when L is a valence bond, Q$_2$ is

H  OH, $R_{22}$ is

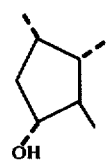

$R_{25}$ is n-pentyl, $R_{30}$ is —COOCH$_3$, and X is trans-s—CH=CH—, and is a compound represented by the formula:

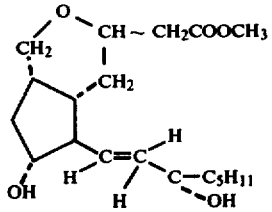 IV

Formula III represents 9-deoxy-6ξ,9α-epoxymethano-17-phenyl-2,18,19,20-tetranor-PGF$_1$, methyl ester when L is ethylene, Q$_2$ is

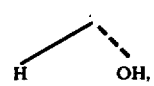

$R_{22}$ is

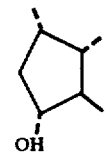

$R_{25}$ is —CH$_2$CH$_2$— 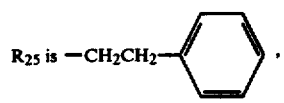, $R_{30}$ is —COOCH$_3$, and X is transCH=CH—, and is a compound represented by the formula

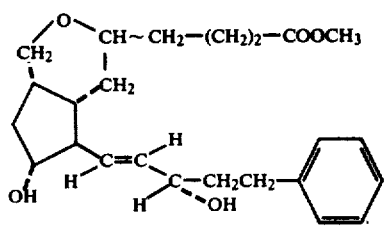 V

Included within the scope of $R_{22}$ in formula III, and following the above nomenclature, are 11β compounds, 11-deoxy-11-oxo (PGD) compounds, 11-deoxy-11-methylene compounds, 11-deoxy compounds, 11-deoxy-10,11-didehydro compounds, and 11-deoxy-11-hydroxymethyl compounds.

Considering the scope of $R_{30}$ in formula III, there are included acids, esters, salts, 2-decarboxy-2-hydroxymethyl compounds, amides, and 2-decarboxy-2-tetrazolyl compounds.

The carbon atoms in the formulae herein are numbered as for prostanoic acid (1), except that the carbon atoms in longer or shorter side chains are named, following the usual convention, as "nor" or "homo" atoms. Thus in compound IV above, the —CH=CH— group is at the "13,14" position and, in the upper side chain, C-2, C-3, and C-4 are "nor" atoms. See N.A. Nelson, J. Medicinal Chem. 17, 911 (1974). Attachment to the $R_{22}$ ring is always at C-8, C-9, and C-12.

For those compounds of formula III wherein $Q_2$ is

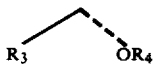

i.e. wherein the C-15 hydroxyl or ether group is attached to the side chain in alpha configuration, the configuration at C-15 is identical to that of the naturally occurring prostaglandins such as $PGE_1$ obtained from mammalian tissues. The 15-epimer compounds are represented by formula III when $Q_2$ is

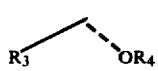

and are identified variously as "15-epi" or "15β, or "15(R)" by the appropriate prefix in the name. As is known in the art, "R" and "S" designations depend on the neighboring substituents. See R. S. Cahn, J. Chem. Ed. 41, 116 (1964).

Included within these formula-III compounds are the isomers wherein ~ is in alpha or beta configuration. The nomenclature for these isomers may refer to "α" or "β" substitution at C-6or, preferably, it may follow the "R" and "S" usage, for which see R. S. Cahn, and N. A. Nelson, cited above.

Although these formulas represent specific optical isomers, it is intended that the compounds are claimed not only in their purified form but also in mixtures, including racemic mixtures or mixtures of the enantiomeric forms.

With regard to formula III, examples of alkyl of one to 4 carbon atoms, inclusive, are methyl, ethyl, propyl, butyl, and isomeric forms thereof. Examples of alkyl of one to 8 carbon atoms, inclusive, are those given above and pentyl, hexyl, heptyl, octyl, and isomeric forms thereof. Examples of alkyl of one to 18 carbon atoms, inclusive, are those given above and nonyl, decyl, undecyl, dodecyl, tridecyl, tetradecyl, pentadecyl, hexadecyl, heptadecyl, octadecyl, and isomeric forms thereof. Examples of cycloalkyl of 3 to 10 carbon atoms, inclusive, which includes alkyl-substituted cycloalkyl, are cyclopropyl,
2-methylcyclopropyl,
2,2-dimethylcyclopropyl,
2,3-diethylcyclopropyl,
2-butylcyclopropyl,
cyclobutyl,
2-methylcyclobutyl,
3-propylcyclobutyl,
2,3,4-triethylcyclobutyl,
cyclopentyl,
2,2-dimethylcyclopentyl,
2-pentylcyclopentyl,
3-tert-butylcyclopentyl,
cyclohexyl,
4-tert-butylcyclohexyl,
3-isopropylcyclohexyl,
2,2-dimethylcyclohexyl,
cycloheptyl,
cyclooctyl,
cyclononyl, and
cyclodecyl.

Examples of aralkyl of 7 to 12 carbon atoms, inclusive, are benzyl,
phenethyl,
1-phenylethyl,
2-phenylpropyl,
4-phenylbutyl,
3-phenylbutyl,
2-(1-naphthylethyl), and
1-(2-naphthylmethyl).

Examples of phenyl substituted by alkyl of one to 4 carbon atoms, inclusive, are (o, m-, or p-)tolyl,
p-ethylphenyl,
p-tert-butylphenyl, and
2,5-dimethylphenyl.

Examples of alkylene of one to 9 carbon atoms, inclusive, with one to 5 carbon atoms, inclusive, in the chain, within the scope of $C_gH_{2g}$ as defined above, are methylene, ethylene, trimethylene, tetramethylene, and pentamethylene, and those alkylene with one or more alkyl substituents on one or more carbon atoms thereof, e.g. —CH(CH$_3$)—, —C(CH$_3$)$_2$—, —CH(CH$_2$CH$_3$)—, —CH$_2$—CH(CH$_3$)—, —CH(CH$_3$)—CH(CH$_3$)—, —CH$_2$—C(CH$_3$)$_2$—, —CH$_2$—CH(CH$_3$)—CH$_3$—, —CH$_2$—CH$_2$—CH(CA$_2$CH$_2$CH$_3$)—, —CH(CH$_3$)—CH(CH$_3$)—CH$_2$—CH$_2$—, —CH$_2$—CH$_2$—CH$_2$—C(CH$_3$)$_2$—CH$_2$, and —CH$_2$—CH$_2$—CH$_2$—CH$_2$—CH(CH$_3$)—. Examples of alkylene of one to 9 carbon atoms, inclusive, substituted with zero, one, or 2 fluoro, with one to 6 carbon atoms in the chain, within the scope of $C_jH_{2j}$ as defined above, are those given above for $C_gH_{2g}$ and hexamethylene, including hexamethylene with one or more alkyl substituents on one or more carbon atoms thereof, and including those alkylene groups with one or 2 fluoro substituents on one or 2 carbon atoms thereof, e.g. —CHF—CH$_2$—, —CHF—CHF—, —CH$_2$—CH$_2$—CF$_2$—, —CH$_2$—CHF—CH$_2$—, —CH$_2$—CH$_2$—CF(CH$_3$)—, —CH$_2$—CH$_2$—CF$_2$—CH$_2$—, —CH(CH$_3$)—CH$_2$—CH$_2$—CH$_2$—CHF—, —CH$_2$—CH$_2$—CH$_2$—CH$_2$—CF$_2$—, —CHF—CH$_2$—CH$_2$—CH$_2$—CH$_2$—CHF—, —CF$_2$—CH$_2$—, CH$_2$—CH$_2$—CH$_2$—CH$_2$—, —CH$_2$—CH$_2$—CH$_2$—CF$_2$—CH$_2$—CH$_2$—, and —CH$_2$—CH$_2$—CH$_2$—CH$_2$—CH$_2$—CF$_2$.

Examples of

as defined above are phenyl,
(o-, m-, or p-)tolyl, (o-, m-, or p-)ethylphenyl,
(o-, m-, or p-)propylphenyl,
(o-, m-, or p-)butylphenyl,
(o-, m-, or p-)isobutylphenyl,
(o-, m-. or p-)tert-butylphenyl,
2,3-xylyl,
2,4-xylyl,
2,5-xylyl,
2,6-xylyl,
3,4-xylyl,
2,6-diethylphenyl,
2-ethyl-p-tolyl,
4-ethyl-o-tolyl,
5-ethyl-m-tolyl,
2-propyl-(o-, m-, or p-)tolyl,
4-butyl-m-tolyl,
6-tert-butyl-m-tolyl,
4-isopropyl-2,6-xylyl,
3-propyl-4-ethylphenyl,
(2,3,4-, 2,3,5-, 2,3,6-, or 2,4,5-)trimethylphenyl,
(o-, m-, or p-)fluorophenyl,
2-fluoro-(o-, m-, or p-)tolyl,
4-fluoro-2,5-xylyl,
(2,4-, 2,5-, 2,6-, 3,4-, or 3,5-)difluorophenyl,
(o-, m-, or p-)chlorophenyl,
2-chloro-p-tolyl,
(3-, 4-, 5-, or 6-)chloro-o-tolyl,
4-chloro-2-propylphenyl,
2-isopropyl-4-chlorophenyl,
4-chloro-3,5-xylyl,
(2,3-, 2,4-, 2,5-, 2,6-3,4-, or 3,5-)dichlorophenyl,
4-chloro-3-fluorophenyl,
(3-, or 4-)chloro-2-fluorophenyl,
α,α,α,-trifluoro-(o-, m-, or p-)tolyl,
(o-, m-, or p-)methoxyphenyl,
(o-, m-, or p-)ethoxyphenyl,
(4- or 5-)chloro-2-methoxyphenyl, and
2,4-dichloro(5- or 6-)methoxyphenyl.

Included in this invention are the pharmacologically acceptable salts when $R_{19}$ in —COOR$_{19}$ of $R_{30}$ is hydrogen. Pharmacologically acceptable salts of these formula-III compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron with within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The novel 5,6-dihydro-prostacyclin-type compounds of formula III have qualitatively the same pharmacological properties described above for prostacyclin or prostacyclin-type compounds and can be used for the same purposes and in the same manner described above. But, quite surprisingly, these novel 5,6-dihydro-prostacyclin-type compounds are substantially more specific with regard to potency in causing prostacyclin-like biological responses. Therefore each of these novel prostacyclin analogs is more useful than prostacyclin for at least one of the pharmacological purposes indicated above. Use of the novel analog for that purpose results in smaller undesired side effects than when prostacyclin is used for the same purpose. Moreover, because of its prolonged activity, fewer and smaller doses of the novel analog can frequently be used to attain the desired result.

These 5,6-dihydro-prostacyclin-type compounds are especially useful for inhibition of platelet aggregation in blood for either in vivo or in vitro applications described above.

To obtain the optimum combination of biological response specificity, potency, and duration of activity, certain compounds within the scope of the formulas III are preferred. For example it is preferred that Q be

wherein it is especially preferred that $R_3$ be hydrogen or methyl, and that $R_4$ be hydrogen.

Another preference for the compounds of formula III is that $R_{19}$ in —COOR$_{19}$ be either hydrogen or alkyl of one to 12 carbon atoms, inclusive, especially one to 4, and more especially methyl or ethyl, for optimum absorption on administration, or a pharmacologically acceptable cation.

For oral administration it is preferred that $R_{30}$ in compounds of formula III be

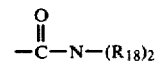

wherein $R_{18}$ is hydrogen, alkyl of one to 12 carbon atoms, inclusive, benzyl, or phenyl, especially hydrogen or alkyl of one to 4 carbon atoms, and more especially hydrogen or methyl, both $R_{18}$'s being the same or different.

When $R_{25}$ in the compounds of formula III is

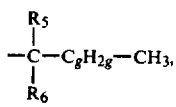

it is preferred that $C_gH_{2g}$ be alkylene of 2, 3, or 4 carbon atoms, and especially that it be trimethylene. It is further preferred that $R_5$ and $R_6$ be hydrogen, methyl, ethyl, or fluoro, being the same or different. It is further preferred, when $R_5$ and $R_6$ are not hydrogen, that both $R_5$ and $R_6$ be methyl or fluoro. It is especially preferred that $R_{25}$ be n-pentyl, 1,1-dimethylpentyl, or 1,1-difluoropentyl.

When $R_{25}$ in the compounds of formula III is

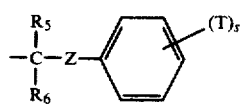

it is preferred that "s" be either zero or one. When "s" is not zero, it is preferred that T be methyl, chloro, fluoro, trifluoromethyl, or methoxy with meta or para attachment to the phenyl ring. When Z is oxa (—O—), it is preferred that $R_5$ and $R_6$ be hydrogen, methyl, or ethyl, being the same or different. It is further preferred, when $R_5$ and $R_6$ are not hydrogen, that both $R_5$ and $R_6$ be methyl. When Z is $C_jH_{2j}$, it is preferred that $C_jH_{2j}$ be a valence bond, methylene, or ethylene. It is especially preferred that $R_{25}$ be

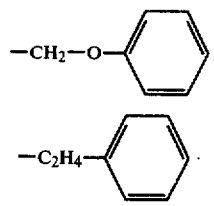

As to variations in $R_{22}$ in the compounds of formulas III, it is preferred that $R_{22}$ be

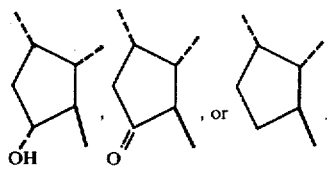

As to variations in L in compounds of formula III, it is preferred that L be —(CH$_2$)$_3$—, —(CH$_2$)'4, or —(CH$_2$)$_5$—and especially —(CH$_2$)$_3$—.

There are also provided mercury compounds of the formula

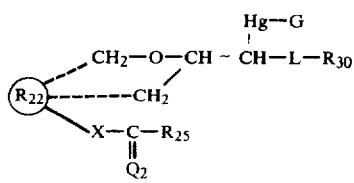

wherein G is nitrato, iodo, chloro, bromo, acetato, trifluoroacetato, or benzoato; and wherein L, $Q_2$, $R_{22}$, $R_{25}$, $R_{30}$, X, and ~ are as defined above.

The novel mercury compounds disclosed herein are useful for pharmacological purposes. They have antiprotozoal and antisyphilitic activity and are consequently effective in treating streptococci and staphylococci. They have antimicrobial activity and are useful for topical antiseptic treatment for animals, including humans, useful domestic animals, pets, zoological specimens, and laboratory animals. They are further useful in ophthalmiatrics.

For these purposes, these mercury compounds are preferably administered topically, for example in alcoholic solution at 0.002 to 0.01% concentration with a benzalkonium chloride as a preservative, or as a lotion, cream, or ointment in 0.5-5.0% concentration in combination with the usual pharmaceutically acceptable diluents. The exact application and concentration depends on such factors as the age, weight and condition of the subject.

Certain mercury compounds within the scope of formula XVI are preferred for optimum biological response specificity, potency, and duration of activity. For example it is preferred that $Q_2$ be

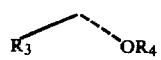

wherein $R_4$ is hydrogen; it is further preferred that L be trimethylene. When $R_3$ is alkyl, it is preferred that $R_3$ be methyl. Likewise, as to $R_{30}$, when $R_{19}$ in —COOR$_{19}$ is alkyl, it is preferred that $R_{19}$ be alkyl of one to 4 carbon atoms, especially methyl. Another preference is that G be chloro or acetato.

The cyclic ethers of formula III are produced by reactions and procedures described and exemplified hereinafter, as shown schematically in the charts.

Chart A will make clear the steps by which a cyclic ether of formula VII is prepared by starting with a 9-deoxy-9-hydroxymethyl-PGF$_2\alpha$ type compound of formula VIII, halogenating and cyclizing the formula-VIII compound to form a compound of formula IX, and subjecting the formula-IX compound to reductive dehalogenation.

CHART A

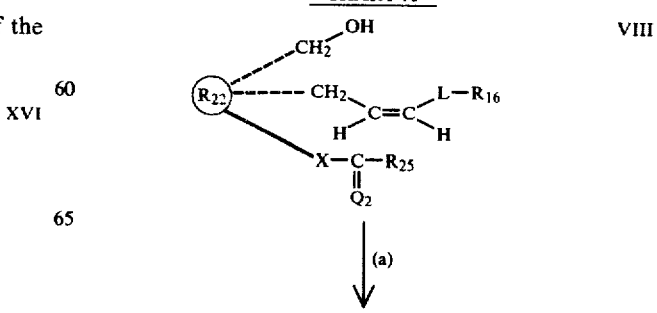

-continued
CHART A

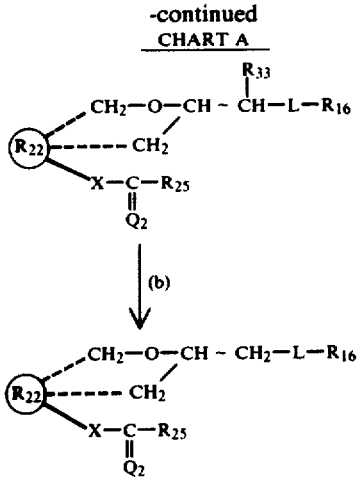

In Chart A, the terms L, $Q_2$, $R_{22}$, $R_{25}$, X, ~, and defined as for compound III above, $R_{16}$ is (1) —$COOR_{17}$
(2) —$CH_2OH$
(3) —$CH_2N(R_{18})_2$

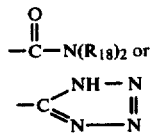

wherein $R_{17}$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl with one, 2, or 3 chloro or alkyl of one to 4 carbon atoms, inclusive, or (g) 2-naphthyl; wherein $R_{18}$ is hydrogen, alkyl of one to 12 carbon atoms, inclusive, benzyl, or phenyl, being the same or different; and $R_{33}$ is iodo or bromo.

The starting materials of formula VIII are 9-deoxy-9-hydroxymethyl derivatives of $PGF_2\alpha$-type compounds known in the art or readily available by processes known in the art. See especially U.S. Pat. No. 3,950,363 as to general methods, and as to 9-deoxy-9α-hydroxymethyl-$PGF_2\alpha$, methyl ester and free acid, and analogs, at columns 14–18, and 34–42, which are incorporated herein by reference. The method of preparation, stated briefly, is to start with a $PGE_2$-type compound previously blocked with silyl groups at C-11 and C-15, and replace the 9-oxo groups with 9-methylene by reaction with a carbanion of an N-alkyl, S-methyl-S-aryl sulfoximine followed by aluminumamalgam reduction, then to block again at C-11 and C-15 with silyl groups, and to transform the 9-methylene group by hydroboration-oxidation to a hydroxymethyl group.

Consequently, the ultimate starting materials for the intermediates of Chart A are $PGE_2$-type compounds which are transformed to the 9-deoxy-9-hydroxymethyl-$PGF_2\alpha$-type compounds of formula VIII. Those $PGE_2$-compounds are within the scope of formula IX:

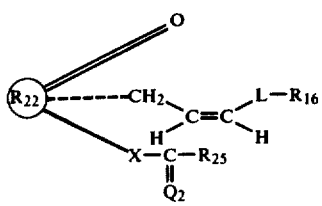

wherein L, $Q_2$, $R_{16}$, $R_{22}$, $R_{25}$, and X are as defined above. For example, as to $PGE_2$, see U.S. Pat. No. 3,598,858; as to 15-methyl-$PGE_2$, see U.S. Pat. No. 3,812,179; as to 15(R)-15-methyl-$PGE_2$, see U.S. Pat. No. 3,804,889; as to $PGE_2$ esters see U.S. Pat. Nos. 3,795,697 and 3,691,216; as to 17,18-didehydro-$PGE_2$, see U.S. Pat. No. 3,598,858; as to 16- and 16,16-dimethyl-$PGE_2$, see U.S. Pat. No. 3,903,131; as to 3-oxa-$PGE_2$, see U.S. Pat. No. 3,944,953; as to 4-oxa-$PGE_2$, see U.S. Pat. No. 3,920,723; as to 3-oxa-17-phenyl-18,19,20-trinor-$PGE_2$, see U.S. Pat. No. 3,931,289; as to $PGE_2$, 15-alkyl ethers, see U.S. Pat. Nos. 3,835,180 and 3,781,325; as to 16- and 16,16-difluoro-$PGE_2$, see U.S. Pat. No. 3,974,189; as to 11β-$PGE_2$, see U.S. Pat. No. 3,931,284; as to 15β-$PGE_2$, see U.S. Pat. No. 3,880,912; as to substituted phenyl esters of $PGE_2$, see U.S. Pat. No. 3,894,062; as to 2a,2b-dihomo-$PGE_2$ compounds, see U.S. Pat. Nos. 3,852,316 and 3,974,195; as to 16-phenoxy-17,18,19,20-tetranor-$PGE_2$, See Derwent Farmdoc No. 73279U and British Spec. No. 1,409,841; as to 17-phenyl-18,19,20-trinor-$PGE_2$, see U.S. Pat. No. 3,987,087; as to 11-deoxy-$PGE_2$, see Derwent Farmdoc No. 10695V and British Spec. No. 1,434,620; as to substituted phenacyl esters, see Derwent Farmdoc No. 16826X and U.S. Pat. No. 3,979,440; as to 2-decarboxy-2-hydroxymethyl compounds, see U.S. Pat. No. 3,636,120; as to C-2 tetrazolyl derivatives, see U.S. Pat. Nos. 3,883,513 and 3,932,389; as to $\Delta_2$-$PGE_2$, see Derwent Farmdoc No. 46497W and German Offenlegungsschrift 2,460,285; as to 11-deoxy-11-hydroxymethyl-$PGE_2$, see U.S. Pat. No. 3,931,282; as to 16-methylene-$PGE_2$, see U.S. Pat. No. 3,953,495; as to 3-(or 4-)oxa-17,18-didehydro-$PGE_2$ compounds, see U.S. Pat. Nos. 3,931,289 and 3,996,266; as to 15-deoxy-$PGE_2$, see Derwent Farmdoc No. 9239W; as to 11-deoxy-15-deoxy-$PGE_2$, see U.S. Pat. No. 3,853,951; as to 13-cis-$PGE_2$, see U.S. Pat. No. 3,932,479; as to 13,14-didehydro-$PGE_2$, see Derwent Farmdoc No. 20717X; as to 2,2-difluoro-$PGE_2$, see U.S. Pat. No. 4,001,300; and as to 11β-17-phenyl-18,19,20-trinor-$PGE_2$, see Derwent Farmdoc No. 13090X.

In step "a" of Chart A, the starting material VIII is subjected to halogenation and cyclization to yield the formula-IX halo compounds. For related cyclization procedures see Stainets and Shilov, Chem. Abs. 64, 12625h (1966). For iodination there is used either an aqueous system containing iodine, potassium iodide, and an alkali carbonate or bicarbonate, or an organic solvent system such as dichloromethane containing iodine in the presence of an alkali metal carbonate. The reaction is carried out at temperatures below 25° C., preferably about 0–5° C. for 10–20 hrs. Thereafter the reaction is quenched with sodium sulfite and sodium carbonate and the formula-IX compound separated from the reaction mixture. For bromination, N-bromosuccinimide or N-bromoacetamide is used. See Fieser et al., Reagents for Organic Synthesis, Vol. 1, pp. 74 and 78, Vol. IV p. 51.

In step "b" of Chart A the halo compound IX is subjected to reductive dehalogenation. Useful reagents include tributyltin hydride, triphenyltin hydride, sodium borohydride in ethanol or dimethyl sulfoxide, and zinc in acetic acid. Especially preferred is tributyltin hydride freshly prepared from tributyltin chloride and lithium aluminum hydride. The reaction is run in a solvent such as benzene at about 15–35° C. and monitored by TLC.

Thereafter, any blocking groups maybe removed by methods known in the art and product VII isolated by methods described herein or known in the art, for example by chromatography on silica gel.

A product within the scope of formula VII may be transformed by methods known in the art or described herein to a product within the scope of formula III. Thus, if $Q_2$ in formula VII is

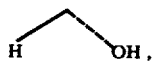

it can be transformed to

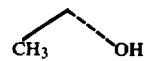

by methods known in the art. See for example U.S. Pat. No. 3,728,382.

As another illustration, if $R_{16}$ in formula VII is —COOCH$_3$, it can be transformed into any one of the substituted phenyl ester groups of —COOR$_{19}$ by first saponifying that methyl ester to yield the free acid and then reesterifying the acid to yield the substituted phenyl ester using methods known in the art. See for example U.S. Pat. No. 3,894,062.

Chart B shows a preferred route to the amides of formula XI and the amines of formula XII. The halo acid XIII is transformed to the halo amide XIV which then yields the amide XI by reductive dehalogenation. On further reduction of the amide, the amine XII is obtained using well-known methods. In Chart B, the terms L, $Q_2$, $R_{22}$, $R_{25}$, $R_{33}$, X, and $\sim$ are as defined above for Chart A; and $R_{18}$ is hydrogen, alkyl of one to 12 carbon atoms, inclusive, benzyl, or phenyl, being the same or different.

Another method of preparing the cyclic ethers within the scope of formula VII as well as others within the scope of formula III is by reductive mercuration of a compound of formula VI shown in Chart C, wherein the terms G, L, $Q_2$, $R_{22}$, $R_{25}$, X, and are as defined above, and $R_{36}$ is the same as $R_{30}$ except that it does not include salts.

Chart C shows the steps by which a 9-deoxy-9-hydroxy-methyl-PGF$_{2\alpha}$-type compound of formula XV is (a) converted to a mercury compound of formula XVI and (b) compound XVI is subjected to reductive demercuration to form the formula-XVII product.

CHART B

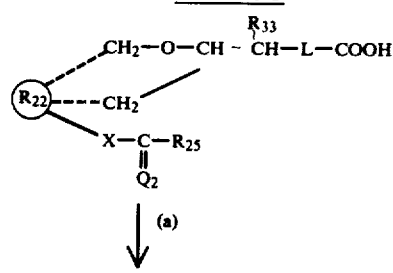
XIII

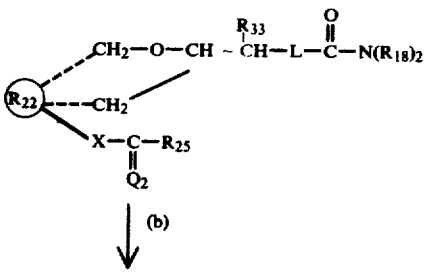
XIV

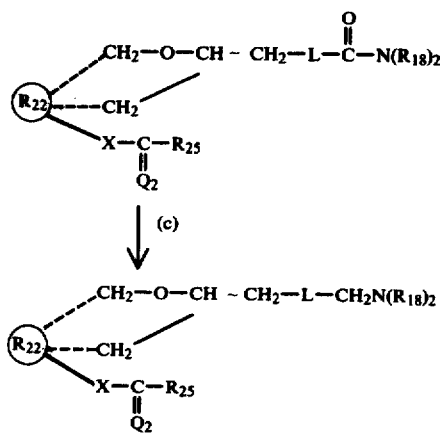
XI

XII

CHART C

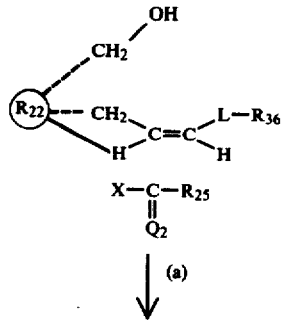
XV

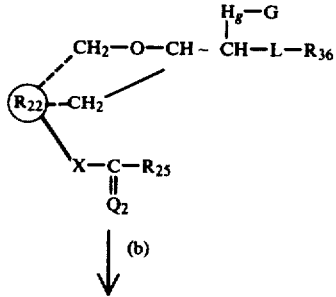
XVI

-continued
CHART C

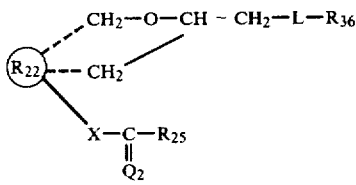

XVII

Reference to Chart C will make clear the steps of this process. For background on this mercuration-demercuration cyclization see, for example, H.C. Brown et al., Organometal. Chem. Syn. 1, 7(1970) and Fieser and Fiewer, Reagents, N.Y., 1972.

The formula-XV starting materials have been discussed above for Chart A. In step "a" of Chart C, the starting material is reacted with an appropriate mercury (II) salt corresponding to Hg(G)$_2$, for example mercuric nitrate, chloride, or acetate. Preferred is either mercuric acetate or trifluoroacetate. The reagent is dissolved in either water or acid, e.g. acetic acid, and combined with a solution of the formula-XV starting material in a solvent such as chloroform or tetrahydrofuran. The reaction is conveniently done at about 15–35° C.

In step "b" of Chart C the mercurio compound is subjected to reductive demercuration. Useful reagents for this step include sodium borohydride, sodium amalgam, and hydrazine. Especially preferred is sodium borohydride in alkaline solution, e.g. aqueous sodium hydroxide. The reaction is carried out in a solvent such as tetrahydrofuran at about 15–35° C. Thereafter the mercury is separated, blocking groups removed if necessary, and the product isolated by methods described herein.

The formula-XVI mercurio compounds are useful not only as intermediates for preparing the formula-XVII products but also for their pharmacological applications as set forth herein. G may be varied, for example, by suitable choice of reagent Hg(G)$_2$ or by replacement, for example of acetate by chloro by ion exchange.

Included in this invention are compounds within the scope of formula III above but in which L is —O—CH$_2$—Y—wherein Y is as defined above, viz. a valence bond or —(CH$_2$)$_k$— wherein k is one or 2. Alternatively L may be simply defined as —O—(CH$_2$)$_n$—CH$_2$— wherein n is zero, one, or 2. Charts D and E show the steps for two processes for obtaining these compounds, illustrated by the formula

XVIII

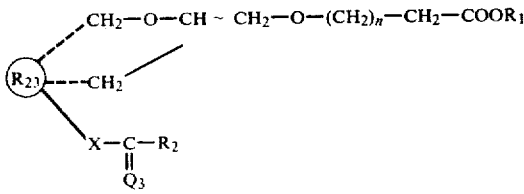

In formula XVIII, R$_1$, R$_2$, X, and ∼ are as defined herein above, "n" is zero, one, or 2 and Q$_3$ is

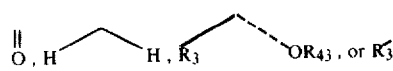

wherein R$_3$ is hydrogen or alkyl of one to 4 carbon atoms, inclusive, and wherein R$_{43}$ is (a) hydrogen, (b) tetrahydropyranyl, tetrahydrofuranyl, 1-ethoxyethyl or a group of the formula

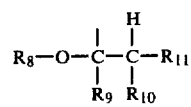

wherein R$_8$ is alkyl of one to 18 carbon atoms, inclusive cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein R$_9$ and R$_{10}$ are the same or different, being hydrogen, alkyl of one to 4 carbon atoms, inclusive, phenyl or phenyl substituted with one, 2, or 3 alkyl of one to 4 carbon atoms, inclusive, or, when R$_9$ and R$_{10}$ are taken together, —(CH$_2$)a— or —(CH$_2$)b—O—(CH$_2$)c— wherein a is 3, 4, or 5, b is one, 2, or 3, and c is one, 2, or 3 with the proviso that b plus c is 2, 3, or 4, and wherein R$_{11}$ is hydrogen or phenyl; (c) a carboxyacyl blocking group

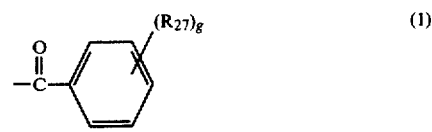

(1)

wherein R$_{27}$ is alkyl of one to 4 carbon atoms, inclusive, phenylalkyl of 7 to 10 carbon atoms, inclusive, or nitro, and g is zero to 5, inclusive, provided that not more than two R$_{27}$'s are other than alkyl, and that the total number of carbon atoms in the R$_{27}$'s does not exceed 10 carbon atoms;

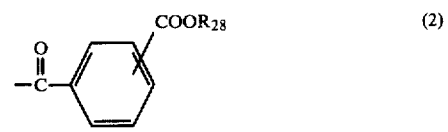

(2)

wherein R$_{28}$ is alkyl of one to 4 carbon atoms, inclusive; or

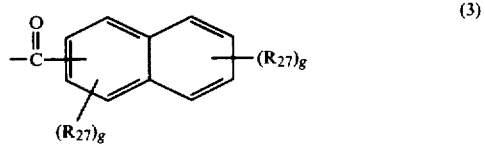

(3)

wherein R$_{27}$ and g are as defined above; or (d) silyl of the formula —Si(R$_{46}$)$_3$ wherein R$_{46}$ is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive, being the same or different. R$_{23}$ is

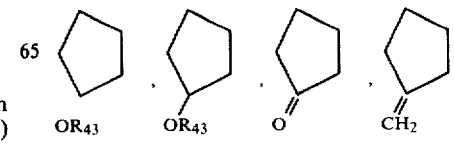

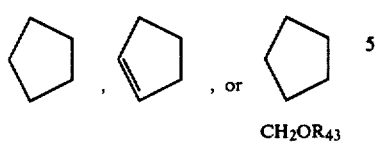
wherein R₄₃ is as defined above.
CHART D
XIX
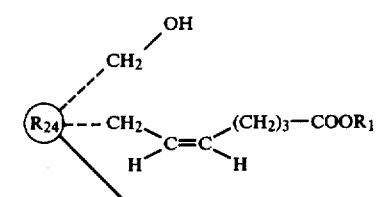
↓ (a)
XX
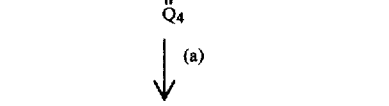
↓ (b)
XXI
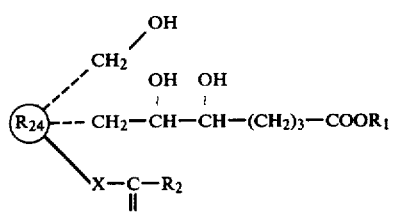
↓ (c)
XXII
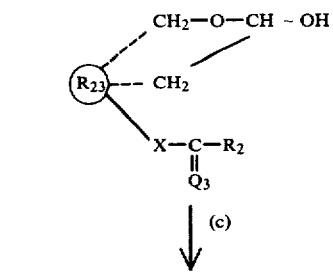
↓ (d)
XXIII
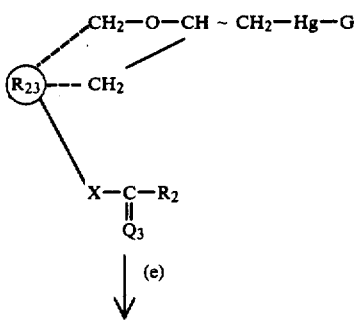
↓ (e)
XXIV
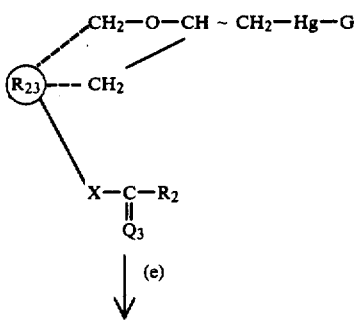
↓ (f)
XXV
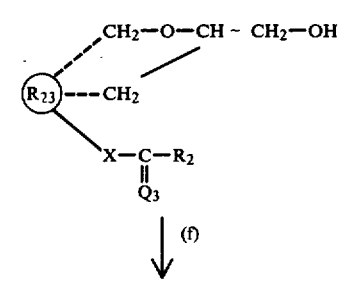
↓ (g)
XVIII
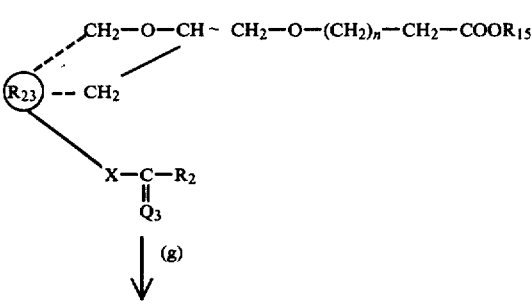
CHART E
XXII
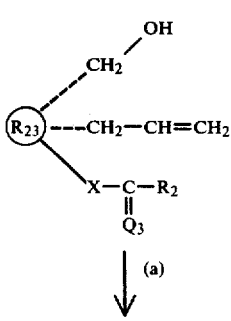
↓ (a)
XXVII -continued

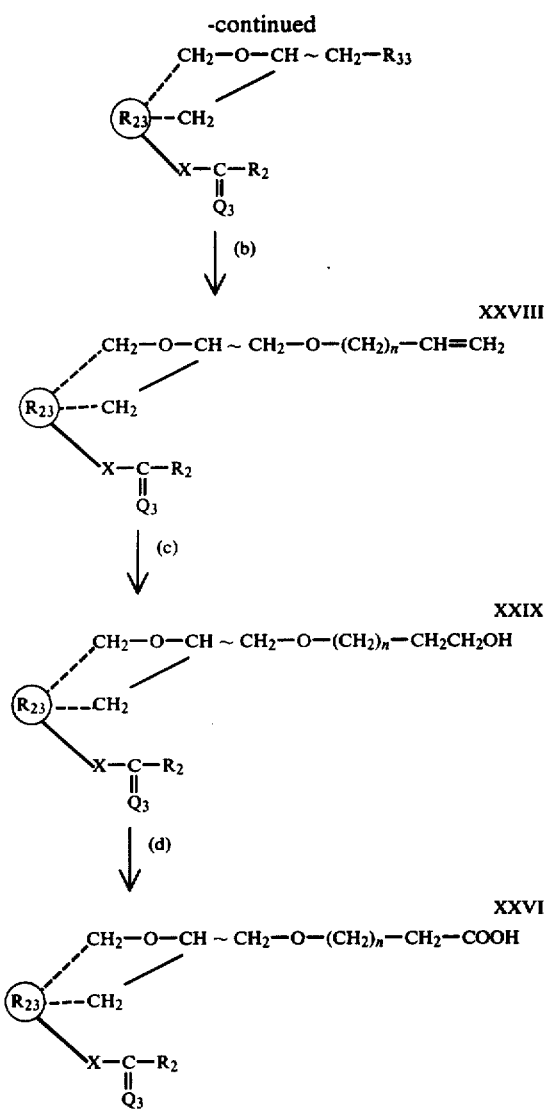

XXVIII

XXIX

XXVI

Chart D shows the steps by which compound XVIII is obtained, starting with a 9-deoxy-9-hydroxymethyl-PGF$_{20}$-type compound XIX, hydroxylating that compound to form glycol XX, transforming that glycol to lactol XXI, condensing that lactol with a Wittig reagent to form vinyl compound XXII, transforming that vinyl compound to mercury compound XXIII, oxidizing that mercury compound to alcohol XXIV, subjecting that alochol to a Williamson synthesis to form XXV and thence by known methods to XVIII.

In Chart D, the terms G, $R_1$, $R_2$, X, and ~ are as used for Charts A-C. The terms "n", $Q_3$, and $R_{23}$ are as defined above for compound XVIII, $Q_4$ is

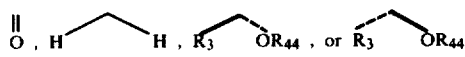

wherein $R_3$ is as defined above and $R_{44}$ is the same as $R_{43}$ except that it does not include hydrogen, and $R_{24}$ is

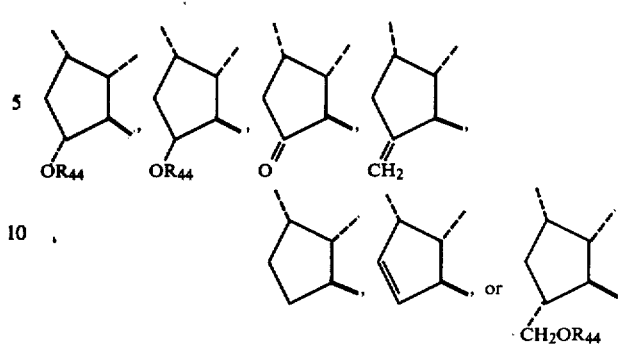

wherein $R_{44}$ is a blocking group as defined above.

The starting materials XIX of Chart D include 9-deoxy-9-hydroxymethyl compounds described herein for Charts A and C and others readily available by methods described herein or known in the art. When $R_{44}$ is carboxyacyl, see U.S. Pat. No. 3,778,450. When $R_{44}$ is silyl, see U.S. Pat. No. 3,892,792.

In step (a) of Chart D the $C_5$-$C_6$ —CH═CH— group is hydroxylated to form glycol XX. The methods are known in the literature, see for example V.VanRheenen et al., Tetrahedron Lett. 1973 (1976). For that step it is preferred that $R_{44}$ be a bulky blocking or protecting group such as t-butyldimethylsilyl or triphenylsilyl.

In step (b) the glycol is cleaved to an aldehyde, for example with sodium periodate in aqueous methanol at 0°-50° C. or with lead tetraacetate in benzene at 0°-50° C. as is known in the art. The aldehyde readily cyclizes to form lactol XXI.

In step (c) the Wittig methylene extension is used, by reaction of the lactol with an ylid derived from $(C_6H_5)_3P$═$CH_2$. For further details of the Wittig reaction see, for example, A. William Johnson, "Ylid Chemistry", Academic Press, N.Y., 1966.

In step (d) the vinyl compound (XXIII) thus obtained is mercurated by known processes, including those described herein for Chart C.

In step (e) the mercury compound (XXIV) is oxidized to the alcohol according to the procedure of G. M. Whitesides. J. Am. Chem. Soc. 96, 870 (1974).

In step (f) the ether compound is formed by a Williamson synthesis employing an ω-halo ester within the scope of

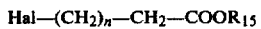

wherein "n" and $R_{15}$ are as defined above and Hal is chloro, bromo, or iodo. Alternatively there is used an orthoester within the scope of

For further information on these known reactions, see, for example, U.S. Pat. No. 3,931,279.

Finally in step (g) the desired product XVIII is obtained by methods known in the art, for example saponification and optional reesterification within the scope of $R_1$ with hydrogen, as by acid hydrolysis for tetrahydropyran-2-yl groups.

Chart E shows the steps by which compound XXVI is obtained, starting with vinyl compound XXII of Chart D, halogenating that vinyl compound to form halo compound XXVII, subjecting that halo compound to a Williamson synthesis to form XXVIII, transforming that compound XXVIII to alcohol XXIX, and oxidizing that alcohol to acid XXVI. Thereafter, if desired, acid XXVI is transformed to esters or other compounds within the scope of formula XVIII herein by methods known in the art.

In Chart E, the terms n, $Q_3$, $R_2$, 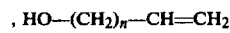 $R_{33}$, X, and ~ are as used in Charts A–D.

In step (a) of Chart E the vinyl compound (XXII of Chart D) is iodinated or brominated using, for example, an aqueous system of iodine-potassium iodide, or N-bromosuccinimide as disclosed herein.

In step (b) compound XXVIII is formed by alkylation with an appropriate alcohol. For example, an alcohol of the formula $$HO-(CH_2)_n-CH=CH_2$$

is dissolved in dimethylformamide, converted to the alkoxide with sodium or sodium hydride, and treated at 0°–100° C. with the formula-XXVII haloether.

In step (c) hydroboration yields the alcohol XXIX, which is readily oxidized to the formula-XXVI acid in step (d), for example with the Jones reagent. See for example U.S. Pat. No. 3,936,487.

Finally, acid XXVI is readily transformed into any one of the compounds within the scope of formula XVIII by methods described herein as known in the art.

Included among the compounds of formulas III and XVIII are 11-methylene compounds. Alternate methods for their preparation, other than those included within Charts A–E above wherein $R_{22}$ or $R_{23}$ is

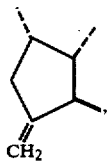

utilize those processes of Charts A–E by replacing starting materials XXXVII, XXXVIII, XXXIX, and XLI with corresponding compounds wherein $R_{22}$ or $R_{23}$ is replaced by

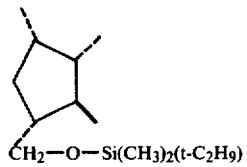

Such compounds are readily prepared from the hydroxymethyl compounds wherein $R_{22}$ or $R_{23}$ is

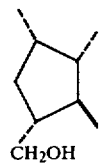

described herein for the starting materials of Chart A, using the procedures of Corey et al. J. Am. Chem. Soc. 94, 6190 (1972).

Thereafter the procedures of Charts A–E yield compounds bearing the t-butyldimethylsilyloxymethyl group at C-11. It is preferred that $R_1$ be alkyl. Next the silyl groups are replaced with hydrogen using tetrabutylammonium fluoride, and the resulting hydroxymethyl groups are converted to iodomethyl groups by way of tosylation and iodide exchange. Finally dehydroiodination, as with potassium tertbutoxide in tetrahydrofuran, yields the 11-methylene compounds.

The intermediates of Charts A–E, including those compounds represented by formulas VI, IX, XIII, XIV, XX, XXI, XXII, XXIII, XXIV, XXV, XXVII, XXVIII, and XXIX, are frequently not isolated but used directly for a subsequent process step. When they are isolated, they are purified by methods known in the art, for example partition extraction, fractional crystallization, and, preferably, silica gel chromatography.

The compounds of Charts A–E wherein $Q_2$, $Q_3$, or $Q_4$ are in either alpha or beta configuration, for example

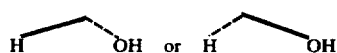

represent 15-α and 15-β isomers. The transformations shown herein generally have no effect on the stereochemistry at this position and therefore the final products have the same stereo configuration at C-15 as in the starting materials at the corresponding carbon atoms. Should it be necessary to separate 15α and 15β isomers, this can be done by methods known in the art, for example by chromatography on neutral silica gel.

When an optically active intermediate or starting material is employed, subsequent steps yield optically active intermediates or products. That optical isomer of 9-deoxy-9-hydroxymethyl-PGF$_2$α compound VIII is preferred which will yield product VII, for example, in the configuration corresponding to that of the naturally occurring prostaglandins. When the racemic form of the intermediate or starting material is employed, the subsequent intermediates or products are obtained in their racemic form. Optically active and racemic forms of the intermediates or starting materials are known or available by methods known in the art.

Compounds within the scope of formulas III and XVIII, herein occur in two isomeric forms wherein ~ is in alpha or beta configuration, i.e. endo or exo relative to the heterocyclic ring. These two isomers differ in their mobility on TLC silica gel plates or on a silica gel column. The members of each pair of isomers are distinguished herein as "less polar" or "more polar" isomers, considering that mobility.

Blocking groups, $R_{40}$, on formula-III or -VII compounds are readily replaced with hydrogen, by acid hydrolysis, for example in dilute acetic acid, aqueous citric acid, or aqueous phosphoric acid-tetrahydrofuran.

Carboxyacyl blocking groups within the scope of $R_{43}$ are removed with an alkali metal carbonate, for example potassium carbonate in methanol at about 25° C. Silyl groups are replaced with hydrogen by prior art procedures disclosed in U.S. Pat. No. 3,892,792 or in Pierce, "Silylation of Organic Compounds", Pierce Chemical Co., Rockford, Ill. (1968).

When the free acid form of the formula-III, -VII, or -XVIII compounds is desired, transformation is brought about by methods known in the art, for example saponification.

Esters are conveniently prepared by interaction of the acid with an appropriate diazohydrocarbon. For example, when diazomethane is used, the methyl esters are produced. Similar use of diazoethane, diazobutane, and 1-diazo-2-ethylhexane for example, gives the ethyl, butyl, and 2-ethylhexyl esters, respectively. Of these esters, methyl or ethyl are preferred.

Esterification with diazohydrocarbons is carried out by mixing a solution of the diazohydrocarbon in a suitable inert solvent, preferably, diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley & Sons, Inc., New York, N. Y., Vol. 8, pp. 389–394 (1954).

An alternative method for esterification of the acid compounds herein comprises transformations of the free acid to the corresponding silver salt, followed by interaction of that salt with an alkyl iodide. Examples of suitable iodides are methyl iodide, ethyl iodide, butyl iodide, and isobutyl iodide. The silver salts are prepared by conventional methods, for example, by dissolving the acid in cold dilute aqueous ammonia, evaporating the excess ammonia at reduced pressure, and then adding the stoichiometric amount of silver nitrate.

Substituted phenyl and naphthyl esters are prepared by methods known in the art. See for example U.S. Pat. No. 3,890,372. Phenacyl-type esters are likewise prepared by methods known in the art. See U.S. Pat. No. 3,979,440.

The lower alkanoates of the formula-III or XVIII compound disclosed herein are prepared from those compounds by replacing any blocking groups ($R_{40}$) with hydrogen, thereafter subjecting the hydroxy compound to a carboxyacylating agent, preferably the anhydride of a lower alkanoic acid, i.e., an alkanoic acid of one to 8 carbon atoms, inclusive. For example, use of acetic anhydride gives the corresponding diacetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 2 to about 10 moles of anhydride per mole of the hydroxy compound reactant. The excess anhydride serves as a reaction diluent and solvent. An inert organic diluent, for example dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride; with acetic anhydride, pyridine, and a 25° C. reaction temperature, a 6 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxylate is recovered from the diethyl ether extract by evaporation. The carboxylate is then purified by conventional methods, advantageously by chromatography.

Compounds within the scope of formulas III, VII, and XVIII are transformed from one to another by methods known in the art. Accordingly, a compound wherein $R_{22}$ is

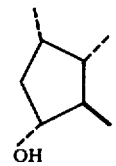

is transformed to another compound wherein $R_{22}$ is another ring within the scope of $R_{22}$, for example an 11-methylene compound, by methods known or described herein. A compound wherein the $C_{13}$-$C_{14}$ group is trans—CH=CH— is transformed to another compound wherein the $C_{13}$-$C_{14}$ group is cis-CH=CH—, —C≡C—, or —CH$_2$CH$_2$—. For example, —C≡C— is obtained by selective bromination and dehydrobromination. A compound wherein the $C_2$ substituent is —COOR$_1$, e.g. a methyl ester, is transformed by known methods to another compound having another $C_2$ substituent within the scope of $R_{30}$, as defined herein, for example —CH$_2$OH or

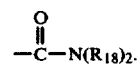

For all of the reactions described herein, the duration of the reaction is readily determined by monitoring with TLC (thin layer chromatography).

DESCRIPTION OF THE PREFERRED EMBODIMENTS

The invention is further illustrated by, but not limited to, the following examples.

All temperatures are in degrees centigrade.

Infrared absorption spectra are recorded on a Perkin-Elmer model 421 infrared spectrophotometer. Except when specified otherwise, undiluted (neat) samples are used.

The NMR spectra are recorded on a Varian A-60, A-60D, T-60, or XL-100 spectrophotometer in deuterochloroform solutions with tetramethylsilane as an internal standard.

Mass spectra are recorded on a Varian Model MAT CH7 Mass Spectrometer a CEC Model 110B Double Focusing High Resolution Mass Spectrometer, or a LKB Model 9000 Gas Chromatograph-Mass Spectrometer (ionization voltage 22 or 70 ev.), and are usually run as TMS (trimethylsilyl) derivatives.

"Brine", herein, refers to an aqueous saturated sodium chloride solution.

"Skellysolve B", herein, refers to mixed isomeric hexanes.

"TLC", herein, refers to thin layer chromatography.

Silica gel chromatography, as used herein, is understood to include elution, collection of fractions, and combination of those fractions shown by TLC to contain the desired product free of starting material and impurities.

"Concentrating", as used herein, refers to concentration under reduced pressure, preferably at less than 50 mm. Hg. and at temperatures below 35° C.

"Lower alkanoate", herein, refers to an ester of an alkanoic acid of one to 8 carbon atoms, inclusive.

Preparation 1

2-Decarboxy-2-amino-PGF Compounds

The following description is provided from a commonly-owned, prior-filed U.S. Patent Application which will be incorporated by reference when that application matures in an issued patent.

Chart M shows the steps by which the formula Cl, $PGF_{2\alpha}$- or 11-deoxy-$PGF_{2\alpha}$-type free acid is transformed to the various 2-decarboxy-2-aminomethyl or 2-decarboxy-2-(substituted amino)methyl-$PGF_\alpha$- or 11-deoxy-$PGF_\alpha$-type compounds of formulas CIV, CVI, CVII, CVIII, CIX, or CX.

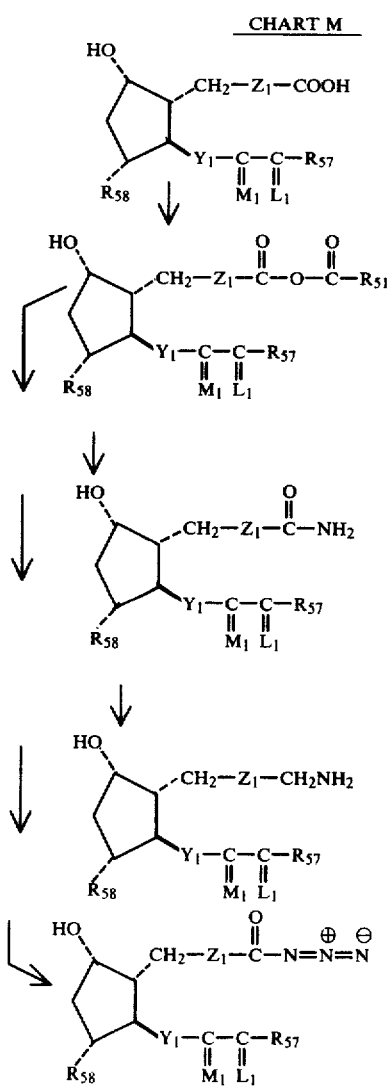

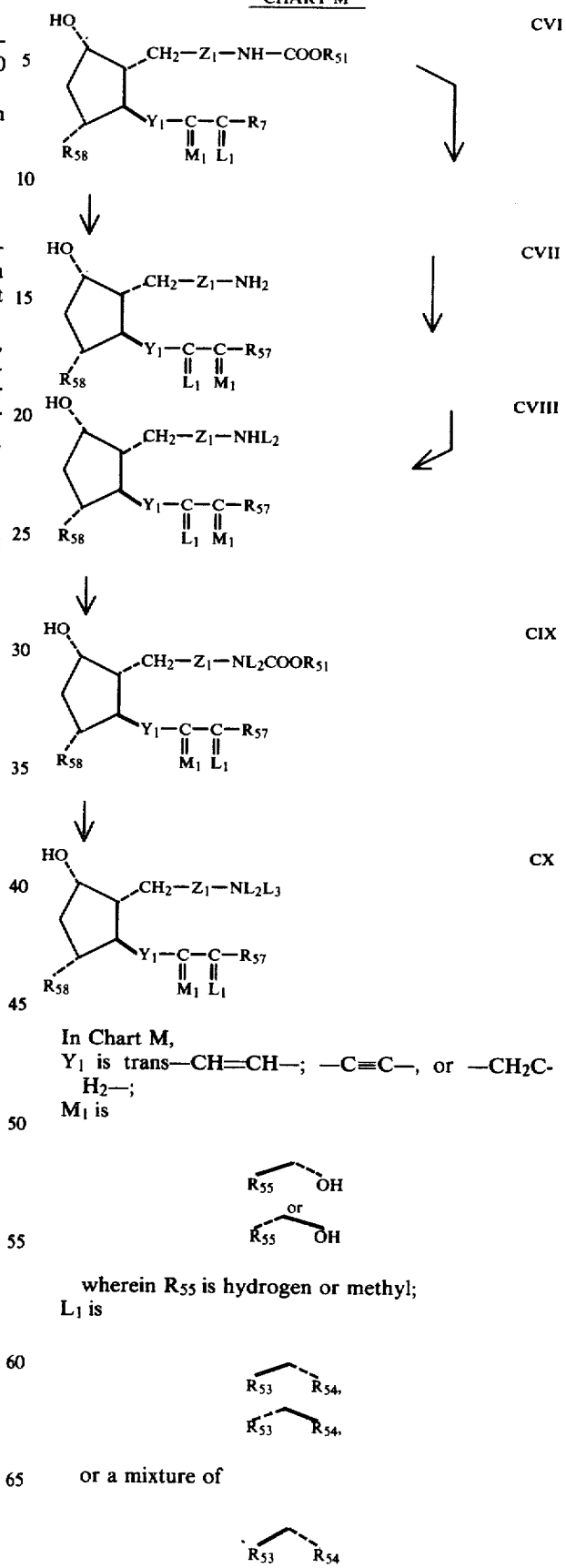

In Chart M,
$Y_1$ is trans—CH=CH—; —C≡C—, or —$CH_2CH_2$—;
$M_1$ is wherein $R_{55}$ is hydrogen or methyl;
$L_1$ is or a mixture of -continued
and

wherein $R_{53}$ and $R_{54}$ are hydrogen, methyl, or fluoro, being the same or different, with the proviso that one of $R_{53}$ and $R_{54}$ is fluoro only when the other is hydrogen or fluoro;

$Z_1$ is
(1) cis—CH=CH—CH$_2$—(CH$_2$)$_g$—CH$_2$—,
(2) cis—CH=CH—CH$_2$—(CH$_2$)$_g$—CF$_2$—,
wherein g is one, 2, or 3;

$R_{57}$ is
(1) —(CH$_2$)$_m$—CH$_3$,

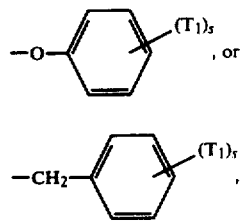

wherein m is one to 5, inclusive, $T_1$ is chloro, fluoro, trifluoromethyl, alkyl of one to 3 carbon atoms, inclusive, or alkoxy of one to 3 carbon atoms, inclusive, and s is zero, one, 2, or 3, the various $T_1$'s being the same or different, with the proviso that not more than two $T_1$'s are other than alkyl, with the further proviso that $R_{59}$ is

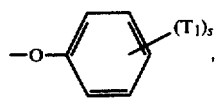

wherein $T_1$ and s are as defined above, only when $R_{53}$ and $R_{54}$ are hydrogen or methyl, being the same or different;

$R_{58}$ is hydrogen or hydroxy;

$L_2$ and $L_3$ are hydrogen, alkyl of one to 4 carbon atoms, inclusive, or —COOR$_{51}$, wherein $R_{51}$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted one, 2, or 3 chloro or alkyl of one to 3 carbon atoms, inclusive; being the same or different, with the proviso that not more than one of $L_2$ and $L_3$ is —COOR$_{51}$.

By the procedure of Chart M the formula CI compound is transformed to a formula CII mixed acid anhydride. These mixed anhydrides are conveniently prepared from the corresponding alkyl, aralkyl, phenyl, or substituted phenyl chloroformate in the presence of an organic base (e.g., triethylamine). Reaction diluents include water in combination with water miscible organic solvents (e.g., tetrahydrofuran). This mixed anhydride is then transformed to either the formula CIII PG-type, amide or formula CV PG-type,azide.

For preparation of the PGF$_{2\alpha}$-type, amide (formula CIII) the formula CII mixed acid anhydride is reacted with liquid ammonia or ammonium hydroxide.

Alternatively, the formula CIII compound is prepared from the formula CI free acid by methods known in the art for transformation of carboxy acids to corresponding carboxyamides. For example, the free acid is transformed to a corresponding methyl ester (employing methods known in the art; e.g., excess ethereal diazomethane), and a methyl ester thus prepared is transformed to the formula CIII amide employing the methods described for the transformation of the formula CII mixed acid anhydride to the formula CIII amide.

Thereafter the formula CIV 2-decarboxy-2-aminomethyl-PGF$_{2\alpha}$- or 11-deoxy-PGF$_{2\alpha}$-type compound is prepared from the formula CIII compound by carbonyl reduction. Methods known in the art art are employed in this transformation. For example, lithium aluminum hydride is conveniently employed.

The formula CII compound is alternatively used to prepare the formula CV azide. This reaction is conveniently carried out employing sodium azide by methods known in the art. See for example, Fieser and Fieser, Reagents for Organic Synthesis vol. 1, pgs. 1041-1043, wherein reagents and reaction conditions for the azide formation are discussed.

Finally, the formula CVI urethane is prepared from the formula CV azide reaction with an alkanol, aralkanol, phenol, or substituted phenol. For example, when methanol is employed the formula CVI compound is prepared wherein $R_1$ is methyl. This formula CVI PG-type product is then employed in the preparation of either the formula CVII or CVIII product.

In the preparation of the formula CVII primary amine from the formula CVI urethane, methods known in the art are employed. Thus, for example, treatment of the formula CVII urethane with strong base at temperatures above 50° C. are employed. For example, sodium potassium, or lithium hydroxide is employed.

Alternatively, the formula CVI compound is employed in the preparation of the formula CVIII compound. Thus, when $L_1$ is alkyl the formula CVIII compound is prepared by reduction of the formula CVI urethane wherein $R_1$ is alkyl. For this purpose, lithium aluminum hydride is the conveniently employed reducing agent.

Thereafter, the formula CVIII product is used to prepare the corresponding CIX urethane by reaction of the formula CVIII secondary amine (wherein $L_2$ is alkyl) wth an alkyl chloroformate. The reaction thus proceeds by methods known in the art for the preparation of carbamates from corresponding secondard amines. Finally, the formula CX product wherein $L_2$ and $L_3$ are both alkyl is prepared by reduction of the formula CIX carbamide. Accordingly, methods hereinabove described for the preparation of the formula CVIII compound from the formula CVI compound are used.

Preparation 1A

2-Decarboxy-2-azidomethyl-PGF$_{2\alpha}$ (1) A solution of t-butyldimethylsilyl chloride (10 g.), imidazole (9.14 g.), and PGF$_{2\alpha}$ (3 g.) in 12 ml. of dimethylformamide are magnetically stirred under nitrogen atmosphere for 24 hr. The resulting mixture is then cooled in an ice bath and the reaction quenched by addition of ice water. The resulting mixture is then diluted with 150 ml. of water and extracted with diethyl ether. The combined ethereal extracts are then washed with water, saturated ammonium chloride, a sodium chloride solution, and thereafter dried over sodium sulfate. Solvent is removed under vacuum yielding PGF$_{2\alpha}$, t-butyldimethylsilyl ester, 9,11,15-tris-(t-butyldimethylsilyl ether). NMR absorptions are observed at 0.20, 0.30, 0.83, 0.87, 0.89, 1.07–2.50, 3.10–4.21, and 5.38 δ. Characteristic infrared absorptions are observed at 970, 1000, 1060, 1250, 1355, 1460, 1720, and 2950 cm.$^{-1}$.

(2) To a magnetically stirred suspension of lithium aluminum hydride (7.75 g.) in 18 ml. of diethyl ether is added dropwise at room temperature over a period of 12 min. 8.71 g. of the reaction product of part (1) above in 40 ml. of diethyl ether. After stirring at ambient temperature for one hr., the resulting product is cooled in an ice water bath and saturated sodium sulfate is added dropwise until the appearance of a milky suspension. The resulting product is coagulated with sodium sulfate, triturated with diethyl ether, and the solvent is removed by suction filtration. Concentration of the diethyl ether under vacuum yields 7.014 g. of 2-decarboxy-2-hydroxymethyl-PGF$_{2\alpha}$, 9,11,15-tris-(t-butyldimethylsilyl ether). NMR absorptions are observed at 0.03, 0.82, 0.87, 1.10–2.60, 3.30–4.30, and 5.37 δ. Characteristic infrared absorptions are observed at 775, 840, 970, 1065, 1250, 1460, 2895, 2995, and 3350 cm$^{-1}$.

(3) p-Toluenesulfonyl chloride (3.514 g.), pyridine (44 ml.), and the reaction product of subpart (2), 7.014 g., are placed in a freezer at −20° C. for 3 days. Thereafter, 7.200 g. of 2-decarboxy-2 -p-toluenesulfonyloxymethyl-PGF$_{2\alpha}$, 9,11,15-tris-(t-butyldimethylsilyl ether), is recovered. NMR absorptions are observed at 0.10, 0.94, 0.97, 1.10, 2.50, 2.50, 4.03, 3.80–4.80, 5.45, 7.35, and 7.80 δ. Infrared absorptions are observed at 775, 970, 1180, 1190, 1250, 1360, 1470, 2900, and 2995 cm$^{-1}$.

(4) The reaction product of subpart (3) (2.13 g.) is placed in 42 ml. of acetic acid, tetrahydrofuran, and water (3:1:1) containing 0.25 ml. of 10 percent aqueous hydrochloric acid. The reaction mixture becomes homogeneous after vigorous stirring for 16 hr. at room temperature. The resulting solution is then diluted with 500 ml. of ethyl acetate; washed with saturated sodium chloride and ethyl acetate; dried over sodium sulfate; and evaporated under reduced pressure, yielding 1.301 g. of an oil. Crude product is chromatographed on 150 g. of slica gel packed with ethyl acetate. Eluting with ethyl acetate yields 0.953 g. of 2-decarboxy-2-p-toluenesulfonyloxymethyl-PGF$_{2\alpha}$.

(5) The reaction product of subpart (4), (0.500 g.) in 5.0 ml. of dimethylformamide was added to a stirred suspension of sodium azide (1.5 g.) in 20 ml. of dimethylformamide. Stirring is continued at ambient temperature for 3 hr. The reaction mixture is then diluted with water (75 ml.), extracted with diethyl ether (500 ml.), and the the etheral extracts washed successively with water, saturated sodium chloride, and dried over sodium sulfate. Removal of the diethyl ether under reduced pressure yields 0.364 g. of 2-decarboxy-2-azidomethyl-PGF$_{2\alpha}$. A characteristic azido infrared absorption is observed at 2110 cm.$^{-1}$.

Preparation 1B

2-Decarboxy-2-aminomethyl-PGF$_{2\alpha}$ (Formula CXXV)

Crude 2-decarboxy-2-azidomethyl-PGF$_{2\alpha}$ (Prep. 1A, 0.364 g.) in 12 ml. of diethyl ether is added to a magnetically stirred suspension of lithium aluminum hydride (0.380 g.) in 20 ml. of diethyl ether. Reaction temperature is maintained at about 0° C. and addition of lithium aluminum hydride proceeds dropwise over a 4 min. period. After addition is complete, the resulting mixture is stirred at ambient temperature for 1.5 hr. and thereafter placed in an ice both (0–5° C.). Excess reducing agent is then destroyed by addition of saturated sodium sulfate. After cessation of gas evolution, the resulting product is coagulated with sodium sulfate, triturated with diethyl ether, and solid salts removed by filtration. The filtrate is then dried with sodium sulfate, and evaporated under reduced pressure to yield 0.304 g. of a slightly yellow oil. This oil (100 mg.) is then purified by preparative thin layer chromatography, yielding 42 mg. of title product. NMR absorptions are observed at 0.90, 1.10–2.80, 3.28, 3.65–4.25, and 5.45 δ. Characteristic infrared absorptions are observed at 970, 1060, 1460, 2995, and 3400 cm.$^{-1}$. The mass spectrum shows parent peak at 699.4786 and other peaks at 628, 684, 595, 217, and 274.

EXAMPLE 1

9-Deoxy-6ξ,9α-epoxymethano-PGF$_1$, Methyl Ester, Mixed Isomers (Formula VII)

1. Refer to Chart A, and consider R$_4$ on (R$_{22}$) and Q$_2$ to be hydrogen. There is first prepared the formula-IX halo compound. A solution of 9-deoxy-9-hydroxymethyl-PGF$_{2\alpha}$, methyl ester (U.S. Pat. No. 3,950,363, 9.3 g.) in 125 ml. of dichloromethane, cooled in an ice bath, is treated with anhydrous sodium carbonate (5.3 g.) and iodine (6.35 g.) and stirred for one hour. Then it is allowed to warm up to 25° C. while stirring for 16 hours. The reaction mixture is diluted with 250 ml. of dichloromethane and then 100 ml. of 10% aqueous sodium sulfite is added. When the iodine color disappears the organic phase is separated, and the aqueous phase is extracted with dichloromethane. The organic phases are combined, washed with brine, dried over sodium sulfate, and concentrated. The resulting oil is subjected to silica gel chromatography, eluting with acetone (20–50%)-dichloromethane, to yield the formula-IX 5-iodo-9-deoxy-6ξ,9α-epoxymethano-PGF$_1$, methyl ester, mixed isomers.

II. Next, the formula-VII title compound is prepared. A solution of the above formula-IX 5-iodo compound (1.0 g.) in 10 ml. of benzene is treated at about 15° C. with 5 mg. of 2,2-azobis-(2-methylpropionitrile) and a solution of 0.58 g. of tributyltin hydride in 4 ml. of diethyl ether added dropwise over about 2 min. The mixture is allowed to warm to about 25° C. while stirring for 1.25 hr. Another portion of tributyltin hydride (0.58 g.) is added and stirring continued for 0.75 hr. The reaction mixture is concentrated, then diluted with 25 ml. of Skellysolve B and 25 ml. of water, stirred for 0.5 hr. and filtered through diatomaceous earth. The aqueous phase, together with aqueous washes of the organic phase, is mixed with 50 ml. of ethyl acetate, saturated with sodium chloride, and stirred for 0.5 hr. The organic phase, together with ethyl acetate washes of the aqueous phase and including the solution in Skellysolve B, is dried over sodium sulfate and concentrated. The resulting oil is subjected to silica gel chromatography, eluting with acetone (25–50%)-dichloromethane, to yield the formula-VII title compound, mixed isomers.

EXAMPLE 2

5ξ-Iodo-9-deoxy-6ξ,9α-epoxymethano-PGF$_1$,

Methyl Ester, Mixed Isomers (Formula IX)

A suspension of 9-deoxy-9-hydroxymethyl-PGF$_{2\alpha}$, methyl ester (U.S. Pat. No. 3,950,363, 100 mg.) in 0.8 ml. of water, cooled in an ice bath, is treated successively with sodium carbonate (12 mg.), potassium iodide (36 mg.) and iodine (55 mg.), and then stirred for 1.5 hours. Then 5 ml. of methylene chloride is added and stirring continued for one hour. The mixture is decolorized with 10% aqueous sodium sulfite and the organic phase separated. The aqueous phase is extracted with methylene chloride and the organic phases are combined, dried over sodium sulfate, and concentrated. The residue is chromatographed on a high pressure silica gel column, eluting with ethyl acetate (10–70%) hexane to yield the title compound mixed isomers, 30 mg., having Rf 0.11 (TLC on silica gel in ethyl acetate-Skellysolve B (4:6)), NMR peaks at 5.4–5.7, 3.65, and 3.6–4.3 δ, and mass spectral peaks at 637, 621, 581, 562, 525, 524, 491, 465, 453, 199, and 173, with the high resolution peak at 652.2487 (TMS derivative).

EXAMPLE 3

5ξ-Iodo-9-deoxy-6ξ,9α-epoxymethano-PGF$_1$, Mixed Isomers (Formula IX)

A solution of the formula-IX 5ξ-iodo-9-deoxy-6ξ,9α-epoxymethano-PGF$_1$, methyl ester, mixed isomers (Example 2, 1.03 g.) in 25 ml. of methanol is treated at about 0° C. with 20 ml. of 3 N aqueous sodium hydroxide. After 15 min. the cooling bath is removed and stirring continued for 2 hr. Crushed ice is added, together with aqueous potassium hydrogen sulfate to acidify. The mixture is extracted with ethyl acetate and the organic phase is washed with brine, dried over magnesium sulfate, and concentrated. The residue is subjected to silica gel chromatography using acid-washed silica gel, eluting with acetone (40–100%)-methylene chloride, to yield the title compoound, consisting of mixed isomers.

EXAMPLE 4

5ξ-Iodo-9-deoxy-6ξ,9α-epoxymethano-PGF$_1$, Methyl Ester, less Polar Isomer and More Polar Isomer (Formula IX)

Refer to Chart A. A solution of 9-deoxy-9-hydroxymethyl-PGF$_2$α, methyl ester (100 mg.) in 2 ml. of methylene chloride is treated with sodium carbonate (56 mg.) and cooled in an ice bath. There is then added iodine (67 mg.) and the mixture stirred at 0° C. for 3 hr., then at about 25° C. for 19 hr. Thereafter 10% aqueous sodium sulfite is added to decolorize the mixture. The organic phase is separated and combined with a methylene chloride extract of the aqueous phase. The organic phase is concentrated and the residue is chromatographed on a high pressure silica gel column, eluting with ethyl acetate (60–80%)-hexane to yield (a) the less polar title compound, 55 mg. having Rf 0.58 (TLC on silica gel in ethyl acetate), (b) mixed isomers, 12 mg., (c) the more polar title compound, 13 mg., having Rf 0.47 (TLC on silica gel in ethyl acetate), and (d) starting material, 18 mg.

EXAMPLE 5

5ξ-Iodo-9-deoxy-6ξ,9α-epoxymethano-PGF$_1$, Methyl Ester, less Polar Isomer and More Polar Isomer (Formula IX)

A suspension of 9-deoxy-9-hydroxymethyl-PGF$_2$α, methyl ester (3.1 g.) in 60 ml. of water is treated with sodium carbonate (1.7 g.) and cooled in an ice bath. To the resulting solution is added potassium iodide (2.7 g.) and iodine (4.14 g.) and stirring continued for 3 hr. at about 0° C. Thereafter, sodium sulfite (2.5 g.) and sodium carbonate (0.8 g.) are added to decolorize the mixture. After a few minutes the mixture is extracted with chloroform. The organic phase is washed with brine, dried over sodium sulfate, and concentrated to yield the mixed isomers of the title compounds, which is further purified by silica gel chromatography, eluting with methylene chloride (15–50%)-acetone to yield the less polar title compound, and the more-polar title compound.

EXAMPLE 6

9-Deoxy-6ξ,9α-epoxymethano-PGF$_1$, Methyl Ester, Less Polar Isomer and More Polar Isomer (Formula VII)

Refer to Chart A. A solution of the less-polar isomer of the formula-IX iodo ether (Example 5, 0.255 g.) in 3 ml. of absolute ethanol is treated with tributyltin chloride (0.12 g.) and then with a freshly prepared solution of sodium borohydride (0.050 g.) in 3 ml. of absolute ethanol. After 45 min. the reaction mixture is diluted with ethyl acetate and water. The organic phase is separated, washed, dried, and concentrated to an oil, consisting of the title compound, less-polar isomer.

Likewise following the above procedure but starting with the more-polar formula-IX iodo ether, there is obtained the title compound, more-polar isomer.

EXAMPLE 7

9-Deoxy-6ξ,9α-epoxymethano-17-phenyl-18,19,20-trinor-PGF$_1$, Methyl Ester Mixed Isomers (Formula VII)

I. Refer to Chart A. There is first prepared the formula-IX 5-iodo compound. A solution of 9-deoxy-9-hydroxymethyl-17-phenyl-18,19,20-trinor-PGF$_1$α, methyl ester (2.4 g.) in 25 ml. of dichloromethane, cooled in an ice bath, is treated with anhydrous sodium carbonate (1.06 g.) and iodine (1.27 g.) and stirred for one hour. Thereafter the mixture is allowed to warm to 25° C., with stirring for 16 hr. The reaction mixture is diluted with 50 ml. of dichloromethane and treated with 20 ml. of 10% aqueous sodium sulfite. After the iodine color has disappeared, the organic phase, together with organic extractions of the aqueous phase with dichloromethane, is dried and concentrated to a pale yellow oil. The oil is subjected to silica gel chromatography to yield the formula-VIII 5-iodo-9-deoxy-6ξ,9α-epoxymethano-17-phenyl-18,19,20-trinor-PGF$_1$, methyl ester, mixed isomers.

II. Next, the formula-VII title compound is prepared. A solution of the above formula-IX 5-iodo compound (1.03 g.) in 9 ml. of benzene is treated with 3 mg. of 2,2-azobis-(2-methyl propionitrile) and to the cold mixture is added 10 ml. of an ether solution of tributyltin hydride (freshly prepared and containing about 0.145 g. per ml.) dropwise over about 5 min. The mixture is allowed to warm to 22°–25° C. and stirred for about 45 min. until the reaction is shown complete by TLC. The mixture is concentrated and the residue stirred with 25 ml. of Skellysolve B and 25 ml. of water for 0.5 hr. The aqueous phase, together with aqueous washes of the Skellysolve B layer, is saturated with sodium chloride and extracted with ethyl acetate. The organic phase, together with ethyl acetate extractions of the aqueous phase, is dried and concentrated to an oil. The oil is subjected to silica gel chromatography, eluting with acetone (20–50%)-dichloromethane to yield the formula-VII title compound, mixed less polar and more polar isomers.

EXAMPLE 8

9-Deoxy-6ξ,9α-epoxymethano-PGF$_1$, Amide, Less Polar and More Polar Isomers (Formula XI)

I. Refer to Chart B. There is first prepared the formula-XIV 5-iodo-9-deoxy-6,9α-epoxymethano-PGF$_1$, amide, less polar and more polar isomers. A solution of the formula-XIII iodo-ether acid, mixed isomers (Example 3, 5.15 g.) in 50 ml. of acetone is cooled to about −10° C. and treated with 3.0 ml. of triethylamine and 3.0 ml. of isobutyl chloroformate. After 5 min. there is added 100 ml. of acetonitrile saturated with ammonia, and the reaction mixture allowed to warm to about 25° C. The mixture is filtered, and the filtrate concentrated. The residue is taken up in ethyl acetate and water. The organic phase is washed with water, dried over magnesium sulfate and concentrated. The residue is subjected to silica gel chromatography, eluting with acetone (25–100%)-methylene chloride. There are obtained the formula-XIV iodo-ether, amide, less polar isomer, a fraction of mixed less and more polar isomers, and the more polar isomer.

II. A mixture of the formula-XIV 5-iodo-9-deoxy-6,9α-epoxymethano-PGF$_1$, amide, mixed isomers (Example 8-I above, 0.49 g.) in 15 ml. of ethanol is treated at about 25° C. with about 0.5 ml. of tributyltin chloride and a mixture of sodium borohydride (0.10 g.) in 5 ml. of ethanol. The reaction is followed by TLC (silica gel in acetone). After about 30 min. additional 0.75 ml. of tributylin chloride is added, and, after further stirring for 45 min., 0.15 g. of sodium borohydride is added, and the reaction continued until complete. The reaction mixture is diluted with ice and water and extracted with ethyl acetate. The organic phase is washed with brine, dried, and concentrated. The residue is subjected to silica gel chromatography, eluting with acetone (50–100%)-methylene chloride. There are obtained fractions consisting of (a) the less polar isomer, (b) a mixture of the less and more polar isomers, and (c) the more polar isomer.

EXAMPLE 9

9-Deoxy-6ξ,9α-epoxymethano-PGF$_1$, Less Polar Isomer and More Polar Isomer (Formula III)

Refer to Chart C. A solution of 9-deoxy-9-hydroxymethyl-PGF$_2\alpha$ (2.05 g.) in 40 ml. of tetrahydrofuran is treated with a mixture of mercuric acetate (3.7 g.), 30 ml. water, and 20 ml. of tetrahydrofuran for 2 hr., with stirring. Thereafter a solution of sodium borohydride (0.75 g.) in 30 ml. of 1 N sodium hydroxide is added in portions within 3 min. After 15 min. the mixture is cooled and cautiously acidified with dilute hydrochloric acid. Diethyl ether and salt (sodium chloride) are added. The organic phase is separated, washed with brine, dried, and concentrated to an oil. The oil is subjected to high pressure liquid chromatography on acetic acid-washed silica gel, eluting with acetone (20–65%)-methylene chloride at approximately 50 pounds per square inch (350 g./cm$^2$). There are obtained four main fractions: (a) the less polar isomer of the title compound, (b) mixed isomers, (c) the more-polar isomer, and (d) recovered unreacted 9-deoxy-9-hydroxy-methyl-PGF$_2\alpha$.

From each of the above isomers, by esterification with diazomethane, there is obtained the corresponding methyl ester having the same properties as that of the corresponding less-polar or more-polar methyl ester of Example 6.

EXAMPLE 10

9-Deoxy-6,9α-epoxymethano-15(S)-15-methyl-PGF$_1$, less polar isomer and more polar isomer (Formula III)

Refer to Chart C. A solution of 9-deoxy-9-hydroxymethyl-15(S)-15-methyl-PGF$_2\alpha$ (U.S. Pat. No. 3,950,363, 3.04 g.) in 60 ml. of tetrahydrofuran is added in portions within 3 min. to a stirred mixture of mercuric acetate (52 g.) in 45 ml. of water and 30 ml. of tetrahydrofuran. After 3 hours stirring, a solution of sodium borohydride (1.1 g.) in 45 ml. of 1 N sodium hydroxide is added in portions. After 15 min. the mixture is cooled and treated with an aqueous solution of potassium hydrogen sulfate to pH 6. Sodium chloride and diethyl ether are added, with stirring for 5 min. The organic phase is separated. The aqueous phase is further acidified to pH 3 and again extracted. The ether extracts are combined, washed with brine, dried, and concentrated to an oil. The oil is subjected to high pressure liquid chromatography on acid-washed silica gel, eluting with acetone (40–60%)-methylene chloride. There are obtained three main fractions: (a) the less-polar isomer of the title compound, (b) mixed isomers, and (c) the more-polar isomer.

Referring to Chart C and following the procedures of Example 10, but replacing the formula-XV starting material of that example with one of the appropriate formula-XV 9-deoxy-9-hydroxymethyl-PGF$_2\alpha$ type compounds, there are obtained the following compounds within the scope of formula III:

9-deoxy-6,9α-epoxymethano-16,16-dimethyl-PGF$_1$, methyl ester, less polar isomer and more polar isomer.

9-deoxy-6,9α-epoxymethano-16,16-dimethyl-PGF$_1$, less polar isomer and more polar isomer 9-deoxy-6,9α-epoxymethano-16-phenoxy-17,18,19,20-tetranor-PGF$_1$, methyl ester, less polar isomer and more polar isomer 9-deoxy-6,9α-epoxymethano-16-phenoxy-17,18,19,20-tetranor-PGF$_1$, less polar isomer and more polar isomer 9-deoxy-6,9α-epoxymethano-17-phenyl-18,19,20-trinor-PGF$_1$, methyl ester, less polar isomer and more polar isomer 9-deoxy-6,9α-epoxymethano-17-phenyl-18,19,20-trinor-PGF$_1$, less polar isomer and more polar isomer 9-deoxy-6,9α-epoxymethano-2-homo-PGF$_1$, methyl ester, less polar isomer and more polar isomer 9-deoxy-6,9α-epoxymethano-2-homo-PGF$_1$, less polar isomer and more polar isomer 9-deoxy-6,9α-epoxymethano-3-oxa-PGF$_1$, methyl ester, less polar isomer and more polar isomer 9-deoxy-6,9α-epoxymethano-3-oxa-PGF$_1$, less polar isomer and more polar isomer 9-deoxy-6,9α-epoxymethano-15-deoxy-PGF$_1$, methyl ester, less polar isomer and more polar isomer 9-deoxy-6,9α-epoxymethano-15-deoxy-PGF$_1$, less polar isomer and more polar isomer 9-deoxy-6,9α-epoxymethano-11-deoxy-PGF$_1$, methyl ester, less polar isomer and more polar isomer 9-deoxy-6,9α-epoxymethano-11-deoxy-PGF$_1$, less polar isomer and more polar isomer

EXAMPLE 11

9-Deoxy-6ξ, 9α-epoxymethano-PGF$_1$, THAM Salt

A solution of the more-polar isomer of the formula-III 9-deoxy-6ξ,9α-epoxymethano-PGF$_1$ (Example 9, 0.092 g.) in 10 ml. of warm acetonitrile is treated while stirring, with a solution of tris(hydroxymethyl)aminomethane (THAM) (0.027 g.) in 1 ml. of dimethyl sulfoxide. The mixture is chilled until a solid separates. The supernatant solution is decanted to yield the title compound.

EXAMPLE 12

9-Deoxy-6ξ,9α-epoxymethano-PGF$_1$, Methyl Ester, 11,15-Diacetate, More Polar Isomer Acetic anhydride (5 ml.) and pyridine (5 ml.) are mixed with 9-deoxy-6,9α-epoxymethano-PGF$_1$, methyl ester, more polar isomer (Example 6, 21 mg.) and the mixture is allowed to stand at 25° C. for 5–18 hr. The mixture is then cooled to 0° C., diluted with 50 ml. of water, and acidified with 5% hydrochloric acid to pH 1. That mixture is extracted with ethyl acetate and the extract is washed successively with 5% hydrochloric acid, 5% aqueous sodium bicarbonate solution, water, and brine, dried and concentrated to give the title compound.

Following the procedure of Example 12, but replacing the acetic anhydride with propionic anhydride, isobutyric anhydride, and hexanoic acid anhydride, there are obtained the corresponding dipropionate, diisobutyrate and dihexanoate derivatives of 9-deoxy-6,9α-epoxymethano-PGF$_1$, methyl ester.

I claim:

1. A cyclic ether of the formula

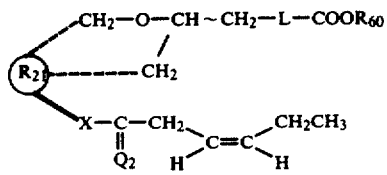

wherein L is (1) a valence bond, (2)—(CH$_2$)$_d$—wherein d is one to 5 inclusive, (3)—(CH$_2$)$_t$—CF$_2$—wherein t is 2, 3, or 4, (4) —CH$_2$—CH=CH—A—wherein A is a valence bond or —(CH$_2$)$_h$—wherein h is one, 2, or 3, or (5) —CH$_2$—O—CH$_2$—Y—wherein Y is a valence bond or —(CH$_2$)$_k$—wherein k is one or 2; wherein Q$_2$ is

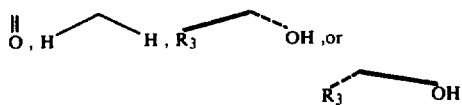

wherein R$_3$ is hydrogen or alkyl of one to 4 carbon atoms, inclusive; wherein (R$_{21}$) is

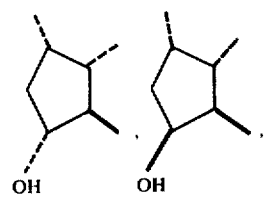

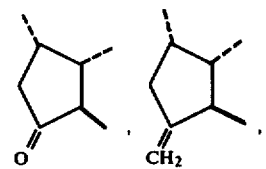

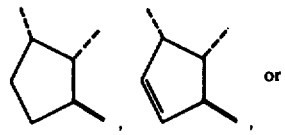

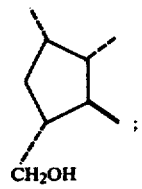

wherein R$_{60}$ is (a) hydrogen, (b) alkyl of one to 12 carbon atoms, inclusive, or (c) a pharmacologically acceptable cation; wherein X is cis- or trans-—CH=CH—, —C≡C—, or —CH$_2$CH$_2$—; and wherein the wavy line (∼) indicates attachment in cis or trans configuration.

2. A compound according to claim 1 wherein X is trans-—CH=CH—.

3. A compound according to claim 2 wherein Q$_2$ is

wherein R$_3$ is hydrogen, methyl, or ethyl.

4. A compound according to claim 3 wherein (R$_{21}$) is

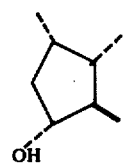

5. A compound according to claim 4 wherein L is —(CH$_2$)$_d$—wherein d is one to 5 inclusive.

6. 9-Deoxy-6ξ,9α-epoxymethano-17,18-didehydro-PGF$_1$, less polar isomer and more polar isomer, compounds according to claim 5.

7. 9-Deoxy-6ξ,9α-epoxymethano-17,18-didehydro-PGF$_1$, methyl ester, less polar isomer and more polar isomer, compounds according to claim 5.

8. A compound according to claim 4 wherein L is —(CH$_2$)$_t$—CF$_2$—where t is 2, 3, or 4.

9. A compound according to claim 4 wherein L is —CH$_2$—O—CH$_2$—Y—wherein Y is a valence bond or —(CH$_2$)$_k$—wherein k is one or 2.

10. A compound according to claim 3 wherein R$_{21}$ is

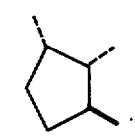

* * * * *